(12) United States Patent
Sun et al.

(10) Patent No.: US 12,203,105 B2
(45) Date of Patent: *Jan. 21, 2025

(54) ENGINEERED STRAIN FOR PRODUCING ALLULOSE AND DERIVATIVES THEREOF, METHOD FOR CONSTRUCTION THEREFOR AND USE THEREOF

(71) Applicant: TIANJIN INSTITUTE OF INDUSTRIAL BIOTECHNOLOGY, CHINESE ACADEMY OF SCIENCES, Tianjin (CN)

(72) Inventors: Yuanxia Sun, Tianjin (CN); Jiangang Yang, Tianjin (CN); Yunjie Li, Tianjin (CN); Yueming Zhu, Tianjin (CN); Chun You, Tianjin (CN); Yanhe Ma, Tianjin (CN)

(73) Assignee: TIANJIN INSTITUTE OF INDUSTRIAL BIOTECHNOLOGY, CHINESE ACADEMY OF SCIENCES, Tianjin (CN)

( * ) Notice: Subject to any disclaimer, the term of this patent is extended or adjusted under 35 U.S.C. 154(b) by 1058 days.

This patent is subject to a terminal disclaimer.

(21) Appl. No.: 15/733,429

(22) PCT Filed: Jan. 25, 2019

(86) PCT No.: PCT/CN2019/073256
§ 371 (c)(1),
(2) Date: Jul. 27, 2020

(87) PCT Pub. No.: WO2019/144944
PCT Pub. Date: Aug. 1, 2019

(65) Prior Publication Data
US 2021/0254031 A1 Aug. 19, 2021

(30) Foreign Application Priority Data
Jan. 25, 2018 (CN) .......................... 201810072372.3

(51) Int. Cl.
| C12N 9/12 | (2006.01) |
| C12N 9/04 | (2006.01) |
| C12N 9/16 | (2006.01) |
| C12N 9/90 | (2006.01) |
| C12N 9/92 | (2006.01) |
| C12P 19/02 | (2006.01) |
| C12P 19/24 | (2006.01) |

(52) U.S. Cl.
CPC ......... *C12N 9/1205* (2013.01); *C12N 9/0006* (2013.01); *C12N 9/12* (2013.01); *C12N 9/16* (2013.01); *C12N 9/90* (2013.01); *C12N 9/92* (2013.01); *C12P 19/02* (2013.01); *C12P 19/24* (2013.01); *C12Y 101/01006* (2013.01); *C12Y 101/01056* (2013.01); *C12Y 207/01002* (2013.01); *C12Y 207/01004* (2013.01); *C12Y 207/01011* (2013.01); *C12Y 301/03039* (2013.01); *C12Y 503/01009* (2013.01)

(58) Field of Classification Search
None
See application file for complete search history.

(56) References Cited

U.S. PATENT DOCUMENTS

| 2002/0106756 A1* | 8/2002 | Bathe ...................... C12P 13/08 |
| | | 435/115 |
| 2010/0317067 A1* | 12/2010 | Kim ...................... C12N 9/1217 |
| | | 435/243 |
| 2020/0131499 A1* | 4/2020 | Wichelecki .... C12Y 504/02002 |

FOREIGN PATENT DOCUMENTS

| CN | 101855357 A | 10/2010 |
| CN | 103333935 A | 10/2013 |
| CN | 103397006 A | * 11/2013 |
| CN | 103468606 A | 12/2013 |
| CN | 103710329 A | 4/2014 |
| CN | 103805552 A | 5/2014 |
| KR | 20170128720 A | * 11/2017 |

OTHER PUBLICATIONS

Park et al. PLoS One 11(7): e0160044, Jul. 28, 2016 (Year: 2016).*
Accession P32719. Oct. 1, 1993. (Year: 1993).*
KR20170128720A. Nov. 23, 2017. Abstract. (Year: 2017).*
CN103397006A. Nov. 20, 2013. Abstact. (Year: 2013).*
Yao, Liping; Metabolic Modification of Glycometabolism for Sucrose to Increase L-Serine Production by Corynebacterium Glutamicum; China Master's Theses Full-Text Database, Engineering Science & Technology I, No. 2, Feb. 15, 2017, pp. B018-249.
Wei, Miao et al.; Effects on Growth and Glycerol Metabolism in E.coli by Coexpression Protein GldA and DhaKLM; Chinese Journal of Bioprocess Engineering, vol. 9, No. (5), Sep. 30, 2011, pp. 59-64.

(Continued)

*Primary Examiner* — Christian L Fronda
(74) *Attorney, Agent, or Firm* — NKL Law; Allen Xue

(57) ABSTRACT

Recombinant strains are obtained for the production of allulose, allose, and allitol by regulating intracellular glucose metabolism, reducing the enzyme activity of fructose 6-phosphate kinase, and enhancing the enzyme activities of glucokinase and glucose-6-phosphate isomerase, allulose 6-phosphate 3-epimerase, allulose 6-phosphate phosphatase, fructose permease and fructokinase, and optionally enhancing the enzyme activities of ribose 5-phosphate isomerase, allose 6-phosphate phosphatase, ribitol dehydrogenase, glycerol permease, glycerol dehydrogenase, and dihydroxyacetone kinase. A method for producing allulose and allose is an extracellular multienzyme cascade method. Multienzyme cascade catalysis and fermentation are coupled to improve the conversion rate of starch sugar or sucrose to the synthesized allulose.

5 Claims, 5 Drawing Sheets
Specification includes a Sequence Listing.

(56) References Cited

OTHER PUBLICATIONS

Granstrom, T.B. et al.; Izumoring: A Novel and Complete Strategy for Bioproduction of Rare Sugars; Journal of Bioscience and Bioengineering, vol. 97, No. (2), Dec. 31, 2004, pp. 89-94.

Izumori, K; Izumoring: A Strategy for Bioproduction of all Hexoses; Journal of Biotechnology, vol. 124, Dec. 31, 2006, pp. 717-722.

Izumori, K. Bioproduction Strategies for Rare Hexose Sugars; Naturwissenschaften, vol. 89, Feb. 16, 2002, pp. 120-124.

Tauch A et al.; Small mobilizable multi-purpose cloning vectors derived from the *Escherichia coli* plasmids pK18 and pK19:selection of defined deletions in the chromosome of Corynebacterium glutamicum; Gene 1994; 145:69-73.

Kirchner Oliver et al.; Tools for genetic engineering in the amino acid-producing bacterium Corynebacterium glutamicum Journal of Biotechnol, 2003, vol. 104, pp. 287-299.

Jakoby,M. et al.; Construction and application of new Corynebacterium glutamicum vectors. Biotechnology Techniques, 1999, vol. 13, pp. 437-441.

\* cited by examiner

ENGINEERED STRAIN FOR PRODUCING ALLULOSE AND DERIVATIVES THEREOF, METHOD FOR CONSTRUCTION THEREFOR AND USE THEREOF

INCORPORATION OF SEQUENCE LISTING

This application contains a sequence listing submitted in Computer Readable Form (CRF). The CFR file containing the sequence listing entitled "8-PA150.0077_ST25.txt", which was created on Jul. 27, 2020, and is 27,085 bytes in size. The information in the sequence listing is incorporated herein by reference in its entirety.

FIELD OF THE INVENTION

The present disclosure belongs to the field of biotechnology, particularly relates to engineered strains for producing allulose and derivatives thereof, methods for construction therefor and use thereof in producing allulose, allose and allitol by fermentation.

BACKGROUND

Rare sugars are a kind of monosaccharides and their derivatives that rarely exist in nature (as defined by the International Society of Rare Sugars (ISRS) in 2002). In recent years, D-allulose, an epimer of fructose, has attracted wide attention in the fields of diet, health care, medicine, etc. D-allulose has 70% of the sweetness of sucrose, but the energy value of D-allulose is only 0.007 kcal/g, and D-allulose has only 0.3% efficiency of energy deposition of sucrose. Therefore, D-allulose is an ideal low calorie sweetener, and can be used as a sucrose substitute in food applications; D-allulose has been proven to have a antihypoglycemic effect, and also inhibit the activities of hepatic fatty synthase and intestinal α-glucosidase thus reducing the abdominal fat deposition, and also has high medical value in the treatment of neurodegenerative and atherosclerotic diseases. The U.S. Food and Drug Administration (FDA) officially approved D-allulose as GRAS in 2011, so that it can be used in a range of foods, pharmaceutical preparations and dietary supplements. Therefore, D-allulose has good application and development prospects.

D-allose and allitol can inhibit the proliferation of various cancer cell lines, which have been proved to be effective in cancer treatment. As antioxidants, D-allose and allitol can have an inhibitory effect on the production of reactive oxygen species (ROS) against oxidative damage, reduce free radical content and delay deterioration. Furthermore, as anti-inflammatory agents, D-allose and allitol can inhibit ischemia-reperfusion injury and segmented neutrophil production, and can be used as cryoprotectant agents for surgery and organ transplantation. Therefore, the rare sugars have both therapeutic and functional food effects, and have great potential for practical applications.

Currently, D-allulose is produced mainly by two methods such as chemical synthesis and bioconversion. The method of chemical synthesis requires multiple protection and deprotection steps, and has high production cost and low product yield. D-allulose is produced using fructose as raw material and under the catalysis of D-allulose 3-epimerase by using the bioconversion method, which is the main approach to synthesize D-allulose at present. However, the conversion rate of the method is low, and the highest conversion rate can only reach 32% currently, which requires simulated moving bed equipment to realize the recycling of fructose, causing that products are not easily separated and that production costs are elevated. Allose is obtained using allulose as a substrate by aldose-ketose isomerization. However, due to the high cost of allulose, the selling prices of allose are very high.

DETAILED DESCRIPTION OF THE INVENTION

In the first aspect of the present disclosure, a method for construction of engineered strains for producing allulose and derivatives thereof, the constructed engineered strains and use thereof are provided, and the method for construction of engineered strains for producing allulose and derivatives thereof includes at least one of the following steps:

(1) enhancing the enzyme activities of glucokinase and glucose 6-phosphate isomerase, for example, increasing the expression strengths of the glucokinase and glucose-6-phosphate isomerase genes by introducing a strong promoter or using an expression plasmid, or integrating the glucokinase and glucose-6-phosphate isomerase genes with higher enzyme activities from other species by using chromosomal integration;

(2) reducing the enzyme activity of fructose 6-phosphate kinase, for example, reducing the expression level of fructose 6-phosphate kinase gene in cells by gene knockout or the introduction of a weak promoter;

(3) enhancing the enzyme activities of allulose 6-phosphate 3-epimerase, allulose 6-phosphate phosphatase, and optionally enhancing the enzyme activities of ribose-5-phosphate isomerase, allose 6-phosphate phosphatase, and ribitol dehydrogenase, for example, introducing genes of allulose 6-phosphate 3-epimerase, allulose 6-phosphate phosphatase and optionally introducing genes of ribose-5-phosphate isomerase, allose 6-phosphate phosphatase, ribitol dehydrogenase into cells by using chromosomal integration or an expression plasmid;

(4) enhancing the enzyme activities of fructose permease and fructokinase, for example, increasing the expression levels of fructose permease and fructokinase genes by using a strong promoter, chromosomal integration or an expression plasmid;

(5) enhancing the enzyme activities of glycerol permease, glycerol dehydrogenase and dihydroxyacetone kinase, for example, increasing the expression levels of glycerol permease, glycerol dehydrogenase and dihydroxyacetone kinase genes by using a strong promoter, chromosomal integration or an expression plasmid.

In the present disclosure, the purpose of enhancing the enzyme activities of glucokinase and glucose 6-phosphate isomerase and reducing the enzyme activity of fructose 6-phosphate kinase is to increase the content of intracellular fructose 6-phosphate; the purpose of enhancing the enzyme activities of allulose 6-phosphate isomerase and allulose 6-phosphate phosphatase is to convert intracellular fructose 6-phosphate into allulose; the purpose of enhancing the enzyme activities of ribose-5-phosphate isomerase and allose 6-phosphate phosphatase is to convert the intracellular allulose 6-phosphate into allose; the purpose of enhancing the enzyme activity of ribitol dehydrogenase is to convert the synthesized allulose into allitol; the purpose of enhancing the enzyme activities of fructose permease and fructokinase is to improve the ability of the engineered strains to convert fructose into fructose 6-phosphate; the purpose of enhancing the enzyme activities of glycerol permease, glycerol dehydrogenase and dihydroxyacetone kinase is to improve the ability of the recombinant strains to metabolize glycerol for cell growth.

According to the present disclosure, the method for construction of engineered strains is suitable for genetic modification by using strains, such as *Corynebacterium glutamate, Escherichia coli, Bacillus subtilis*, Lactic acid bacteria, *Saccharomyces cerevisiae*, as host bacteria. The obtained engineered strains can be used for the synthesis of allulose and derivatives thereof, such as allose or allitol, by fermentation.

In the present disclosure, the culture media for fermentation of the engineered strains are not particularly defined, and may be commonly culture media for bacterial fermentation in the art, such as BHI culture media, TSB culture media, preferably BHI culture media.

According to the present disclosure, in the fermentation system, a carbohydrate compound or glycerol can be used as a substrate, and the carbohydrate compound is selected from, for example, starch and derivatives thereof, sucrose, glucose, and fructose; the initial concentration of the substrate is 1-5%, for example, 2%, 3%, 4%, preferably 2%. According to the present disclosure, the fermentation temperature is 30-37° C., and the fermentation time is 24-48 hours.

In an embodiment of the present disclosure, a method for construction of a recombinant *Corynebacterium glutamicum* strain for producing allulose is provided, including at least one of the following steps:

(1) amplifying the allulose 6-phosphate 3-epimerase (P6PE) gene (SEQ ID No: 1) and the allulose 6-phosphate phosphatase (P6PP) gene (SEQ ID No: 2) derived from *Escherichia coli* and constructing them into the expression vector pEC-XK99E to obtain a recombinant expression vector pEC-P6PE-P6PP, and converting the recombinant expression vector pEC-P6PE-P6PP into wild-type *Corynebacterium glutamicum* ATCC13032 to obtain a recombinant strain Allulose1;

(2) using *Corynebacterium glutamicum* ATCC13032 as the starting strain, reducing the expression level of fructose 6-phosphate kinase gene (SEQ ID No: 3) to obtain a recombinant strain Allulose2;

(3) constructing the recombinant expression vector pEC-P6PE-P6PP bearing the allulose 6-phosphate 3-epimerase and allulose 6-phosphate phosphatase genes into the recombinant strain Allulose2 to obtain a recombinant strain Allulose3;

(4) amplifying the glucokinase gene (SEQ ID No: 4) and glucose 6-phosphate isomerase gene (SEQ ID No: 5) derived from *Corynebacterium glutamicum* and constructing them into the expression vector pXMJ19 to obtain a recombinant plasmid pXMJ19-GlK-PGI, converting the recombinant plasmid pXMJ19-GlK-PGI into the recombinant strain Allulose3 to obtain a recombinant strain Allulose4;

(5) amplifying the fructose permease gene (SEQ ID: 6) from *Zymomonas mobilis* and the fructokinase gene (SEQ ID: 7) derived from *Escherichia coli* or *Enterococcus faecalis*, and constructing them into the expression vector pEC-P6PE-P6PP to obtain a recombinant vector pEC-P6PE-P6PP-FK-GLF, constructing the recombinant plasmid pEC-P6PE-P6PP-FK-GLF and the optional pXMJ19-GLK-PGI into the recombinant strain Alluose2 to obtain a recombinant strain Allulose5;

(6) amplifying the glycerol permease gene (SEQ ID No: 8) derived from *Escherichia coli*, the glycerol dehydrogenase gene (SEQ ID No: 9) from *Klebsiella pneumoniae*, and the dihydroxyacetone kinase gene (SEQ ID No: 10) from *Citrobacter freundii*, and constructing them into the recombinant plasmid pXMJ19-GlK-PGI to obtain a recombinant plasmid pXMJ19-GlK-PGI-GlpF-DhaD-DhaK, converting the recombinant plasmid pXMJ19-GlK-PGI-GlpF-DhaD-DhaK and pEC-P6PE-P6PP-FK-GIF at the same time into the recombinant strain Allulose2 to obtain a recombinant strain Allulose e 6.

In the embodiment, in step (1), the allulose 6-phosphate phosphatase P6PP gene is derived from *Archaeoglobus fulgidus* or *Escherichia coli*, in which the allulose 6-phosphate phosphatase P6PP derived from *Escherichia coli* may not only catalyze the dephosphorylation of allulose 6-phosphate to allulose, but also catalyze the dephosphorylation of allose 6-phosphate to allose.

In the embodiment, in step (2), the expression level of the fructose 6-phosphate kinase gene may be reduced via genetic knockout or replacement of weak promoters. For example, primers may be designed based on the upstream and downstream sequences derived from the fructose 6-phosphate kinase gene, and amplified to obtain amplified fusion gene fragments of fructose 6-phosphate kinase. Gene knockout vectors were constructed and introduced into host cells to obtain the fructose 6-phosphate kinase gene knockout Allulose2. The fructose 6-phosphate kinase gene may be derived from *Corynebacterium* glutamate, the upstream sequence is SEQ ID No: 13, and the downstream sequence is SEQ ID No: 14. For example, the method for replacing weak promoters includes replacing the promoter sequences of the fructose 6-phosphate kinase gene on chromosomes of the cells with weak promoters by homologous recombination, thereby reducing the expression level of the fructose 6-phosphate kinase gene.

The above-mentioned recombinant *Corynebacterium glutamicum* strains Allulose1, Allulose3, Allulose4, Allulose5 and Allulose6 are provided in the present disclosure. The use of the above-mentioned recombinant *Corynebacterium glutamicum* strains Allulose1, Allulose3, Allulose4, Allulose5 and Allulose6 in producing allulose is also provided.

In a particular embodiment, recombinant strains Allulose1 and Allulose3 are used to ferment glucose to synthesize allulose. Recombinant strains Allulose4 and Allulose5 can ferment glucose, fructose, sucrose or a mixture of the above three, such as molasses, to produce allulose. Recombinant strain Allulose6 not only can ferment glucose, fructose, sucrose or a mixture of the above three, such as molasses, to produce allulose, but also can ferment glycerol or a mixed culture medium of glucose and glycerol to produce allulose. In another embodiment of the present disclosure, a method for construction of recombinant *Corynebacterium glutamicum* strains for producing allose is provided, including the following steps: further introducing the ribose-5-phosphate isomerase gene into the above-mentioned allulose producing strains.

Specifically, the method for construction includes at least one of the following steps:

(1) amplifying the allulose 6-phosphate 3-epimerase (P6PE) gene (SEQ ID No: 1), the ribose-5-phosphate isomerase gene (SEQ ID No: 11) and the allulose 6-phosphate phosphatase (P6PP) gene (SEQ ID No: 2) derived from *Escherichia coli* and constructing them into the expression vector pEC-XK99E to obtain a recombinant expression vector pEC-P6PE-RpiB-P6PP, converting the recombinant expression vector pEC- P6PE-RpiB-P6PP into wild-type *Corynebacterium glutamicum* ATCC13032 to obtain a recombinant strain Allose 1;
(2) constructing the recombinant expression vector pEC-P6PE-RpiB-P6PP bearing the allulose 6-phosphate 3-epimerase, ribose-5-phosphate isomerase and allulose 6-phosphate phosphatase genes into the recombinant strain Allulose 2 to obtain a recombinant strain Allose2;
(3) converting the recombinant expression vectors pEC-P6PE-RPIB-P6PP and pXMJ19-GLK-PGI together into the recombinant strain Allulose2 to obtain a recombinant strain Allose3;
(4) converting the recombinant expression vectors pEC-P6PE-RpiB-P6PP and pXMJ19-GlK-PGI-GlpF-DhaD-DhaK together into the recombinant strain Allulose2 to obtain a recombinant strain Allose4.

In the present disclosure, it is unexpectedly found that allulose 6-phosphate phosphatase has catalytic activity for dephosphorylation of allose 6-phosphate during the fermentation process. When the recombinant strains were introduced with the ribose-5-phosphate isomerase gene and the allulose 6-phosphate phosphatase P6PP gene at the same time, the allose yields are significantly higher than those for the recombinant strains introduced with the ribose-5-phosphate isomerase gene only, indicating that allulose 6-phosphate has a catalytic effect on the dephosphorylation of allose 6-phosphate.

The recombinant *Corynebacterium glutamicum* strains Allose1, Allose2, Allose3, and Allose4 constructed by the above-described method are also provided in the present disclosure.

The use of the recombinant *Corynebacterium glutamicum* strains Allose1, Allose2, Allose3, and Allose4 in producing allose is also provided. In a particular embodiment, the recombinant strains Allose1, Allose2 and Allose3 can ferment single or combined of glucose, fructose and sucrose to synthesize allose; the recombinant strain Allose4 can not only ferment single or combined of glucose, fructose and sucrose to synthesize allose, but also ferment glycerol and glucose to synthesize allose.

In another embodiment of the present disclosure, a method for construction of recombinant *Corynebacterium glutamicum* strains for synthesizing allitol is provided, including the following steps: further introducing the ribitol dehydrogenase gene into the above-mentioned Allulose producing strains.

Specifically, the method for construction includes at least one of the following steps:
(1) amplifying the allulose 6-phosphate 3-epimerase gene (SEQ ID No: 1), and the allulose 6-phosphate phosphatase gene (SEQ ID No: 2) derived from *Escherichia coli* and the ribitol dehydrogenase gene (SEQ ID No: 12) from *Klebsiella oxytoca*, and constructing them into the expression vector pEC-XK99E to obtain a recombinant expression vector pEC-P6PE-P6PP-RDH, converting the recombinant expression vector pEC-P6PE-P6PP-RDH into the wild-type *Corynebacterium glutamicum* ATCC13032 to obtain a recombinant strain Allitol1;
(2) constructing the recombinant expression vector pEC-P6PE-P6PP-RDH into the recombinant strain Allulose to obtain a recombinant strain Allitol2;
(3) converting the recombinant expression vectors pEC-P6PE-P6PP-RDH and pXMJ19-GlK-PGI together into the recombinant strain Allulose2 to obtain a recombinant strain Allitol3;
20) (4) converting the recombinant expression vectors pEC-P6PE-P6PP-RDH and pXMJ19-GlK-PGI-GlpF-DhaD-DhaK together into the recombinant strain Allulose2 to obtain a recombinant strain Allitol4.

The recombinant *Corynebacterium glutamicum* strains Allitol1, Allitol2, Allitol3, and Allitol4 constructed by the above-described method are also provided in the present disclosure.

The use of the recombinant *Corynebacterium glutamicum* strains Allitol1, Allitol2, Allitol3, and Allitol4 in producing allitol is also provided. The recombinant strains Allitol1, Allitol2 and Allitol3 can ferment single or combined of glucose, fructose and sucrose to synthesize allitol. The recombinant strain Allitol4 can not only ferment single or combined of glucose, fructose and sucrose to synthesize allitol, but also ferment glycerol and glucose to synthesize allitol.

In the second aspect of the present disclosure, a method for synthesis of allulose and derivatives thereof by extracellular multienzyme catalysis is provided in the present disclosure, including using at least one of starch, starch derivatives, and sucrose, as a substrate, adding a multienzyme complex, and carrying out an enzyme-catalyzed reaction to obtain allulose or allose.

In an embodiment of the present disclosure, a method for the synthesis of allulose from starch and starch derivatives by an extracellular multienzyme cascade reaction is provided, including using starch or starch derivatives as a substrate, adding a multienzyme complex containing glucan phosphorylase, phosphoglucomutase, glucose phosphate isomerase, allulose 6-phosphate 3-epimerase, allulose 6-phosphate phosphatase, isoamylase, and glucan transferase, and carrying out an enzyme-catalyzed reaction to obtain allulose.

The starch and starch derivatives include any one of starch derivatives such as hydrolyzed starch, amylodextrine, maltodextrin, maltopolysaccharide or a mixture of two or more of these starch derivatives in any proportion, and preferably maltodextrin.

In the reaction system, the concentration of starch or starch derivatives is 1-100 g/L, the amount of glucan phosphorylase is 0.1-1000 U/mL, the amount of phosphoglucomutase is 0.1-1000 U/mL, the amount of glucose phosphate isomerase is 0.1-1000 U/mL, the amount of allulose 6-phosphate 3-epimerase is 0.1-1000 U/mL, the amount of allulose 6-phosphate phosphatase is 0.1-1000 U/mL, the amount of isoamylase is 0.1-1000 U/mL, and the amount of glucan transferase is 0.1-1000 U/mL.

Preferably, the concentration of starch or starch derivatives is 50 g/L, the amount of glucan phosphorylase is 10 U/mL, the amount of phosphoglucomutase is 10 U/mL, the amount of glucose phosphate isomerase is 10 U/mL, the amount of allulose 6-phosphate 3-epimerase is 10 U/mL, the amount of allulose 6-phosphate phosphatase is 10 U/mL, the amount of isoamylase is 10 U/mL, and the amount of glucan transferase is 10 U/mL.

During the enzyme-catalyzed reaction, the temperature is 10-80° C., the pH is 5-9, and the reaction time is 1-120 hours. The preferred reaction temperature is 10-40° C., such as 10° C., 20° C., 30° C., 37° C. The preferred reaction pH is 6.5, 7.0, 7.5, 8.0. The preferred reaction time is 48-96 hours, such as 48 hours, 72 hours, 96 hours.

In an embodiment of the present disclosure, a method for conversion of sucrose to allulose by an extracellular multienzyme cascade reaction is provided, including using sucrose as a substrate, adding a multienzyme complex containing sucrose phosphorylase, phosphoglucomutase, glucose phosphate isomerase, allulose 6-phosphate 3-epimerase, allulose 6-phosphate phosphatase, glucose isomerase, glucokinase, and carrying out an enzyme-catalyzed reaction to obtain allulose.

The substrate sucrose not only refers to pure sucrose, but also can be single or combined sucrose-rich raw materials such as sugar cane molasses, soybean molasses, preferably pure sucrose.

In the reaction system, the concentration of sucrose is 1-100 g/L, the amount of sucrose phosphorylase is 0.1-1000 U/mL, the amount of phosphoglucomutase is 0.1-1000 U/mL, the amount of glucose phosphate isomerase is 0.1-1000 U/mL, the amount of allulose 6-phosphate 3-epimerase is 0.1-1000 U/mL, the amount of allulose 6-phosphate phosphatase is 0.1-1000 U/mL, the amount of glucose isomerase is 0.1-1000 U/mL, and the amount of glucokinase is 0.1-1000 U/mL.

Preferably, the concentration of sucrose is 20 g/L, the amount of sucrose phosphorylase is 10 U/mL, the amount of phosphoglucomutase is 10 U/mL, the amount of glucose phosphate isomerase is 10 U/mL, the amount of allulose 6-phosphate 3-epimerase is 10 U/mL, the amount of allulose 6-phosphate phosphatase is 10 U/mL, the amount of glucose isomerase is 10 U/mL, and the amount of glucokinase is 10 U/mL.

During the enzyme-catalyzed reaction, the temperature is 10-80° C., pH is 5-9, and the reaction time is 1-120 hours. The preferred reaction temperature is 10-40° C., such as 10° C., 20° C., 30° C., 37° C. The preferred reaction pH is 6.5, 7.0, 7.5, 8.0. The preferred reaction time is 48-96 hours, such as 48 hours, 72 hours, 96 hours.

In an embodiment of the present disclosure, a method for conversion of starch and starch derivatives to allose by an extracellular multienzyme cascade reaction is provided, including using starch or starch derivatives as a substrate, adding a multienzyme complex containing glucan phosphorylase, phosphoglucomutase, glucose phosphate isomerase, allulose 6-phosphate 3-epimerase, ribose-5-phosphate isomerase, allose 6-phosphate phosphatase, isoamylase, glucan transferase, and carrying out an enzyme-catalyzed reaction to obtain allose.

The starch and starch derivatives include any one of starch derivatives such as hydrolyzed starch, amylodextrine, maltodextrin, maltopolysaccharide or a mixture of two or more of these starch derivatives in any proportion, and preferably maltodextrin.

In the reaction system, the concentration of starch or starch derivatives is 1-100 g/L, the amount of glucan phosphorylase is 0.1-1000 U/mL, the amount of phosphoglucomutase is 0.1-1000 U/mL, the amount of glucose phosphate isomerase is 0.1-1000 U/mL, the amount of allulose 6-phosphate 3-epimerase is 0.1-1000 U/mL, the amount of ribose-5-phosphate isomerase is 0.1-1000 U/mL, the amount of allose 6-phosphate phosphatase is 0.1-1000 U/mL, the amount of isoamylase is 0.1-1000 U/mL, and the amount of glucan transferase is 0.1-1000 U/mL.

Preferably, the concentration of starch or starch derivatives is 50 g/L, the amount of glucan phosphorylase is 10 U/mL, the amount of phosphoglucomutase is 10 U/mL, the amount of glucose phosphate isomerase is 10 U/mL, the amount of allulose 6-phosphate 3-epimerase is 10 U/mL, the amount of ribose-5-phosphate isomerase is 10 U/mL, the amount of allose 6-phosphate phosphatase is 10 U/mL, the amount of isoamylase is 10 U/mL, and the amount of glucan transferase is 10 U/mL.

During the enzyme-catalyzed reaction, the temperature is 10-80° C., the pH is 5-9, and the reaction time is 1-120 hours. The preferred reaction temperature is 10-40° C., such as 10° C., 20° C., 30° C., 37° C. The preferred reaction pH is 6.5, 7.0, 7.5, 8.0. The preferred reaction time is 48-96 hours, such as 48 hours, 72 hours, 96 hours.

In an embodiment of the present disclosure, a method for conversion of sucrose to allose by an extracellular multienzyme cascade reaction is provided, including using starch or starch derivatives as a substrate, adding a multienzyme complex containing sucrose phosphorylase, phosphoglucomutase, glucose phosphate isomerase, allulose 6-phosphate 3-epimerase, ribose-5-phosphate isomerase, allose 6-phosphate phosphatase, isoamylase, glucan transferase. and carrying out an enzyme-catalyzed reaction to obtain allose.

The substrate sucrose not only refers to pure sucrose, but also can be single or combined sucrose-rich raw materials such as sugar cane molasses, soybean molasses, preferably pure sucrose.

In the reaction system, the concentration of sucrose is 1-100 g/L, the amount of sucrose phosphorylase is 0.1-1000 U/mL, the amount of phosphoglucomutase is 0.1-1000 U/mL, the amount of glucose phosphate isomerase is 0.1-1000 U/mL, the amount of allulose 6-phosphate 3-epimerase is 0.1-1000 U/mL, the amount of ribose-5-phosphate isomerase is 0.1-1000 U/mL, the amount of allose 6-phosphate phosphatase is 0.1-1000 U/mL, the amount of glucose isomerase is 0.1-1000 U/mL, and the amount of glucokinase is 0.1-1000 U/mL.

Preferably, the concentration of sucrose is 20 g/L, the amount of sucrose phosphorylase is 10 U/mL, the amount of phosphoglucomutase is 10 U/mL, the amount of glucose phosphate isomerase is 10 U/mL, the concentration of allulose 6-phosphate 3-epimerase is 10 U/mL, the amount of ribose-5-phosphate isomerase is 10 U/mL, the amount of allose 6-phosphate phosphatase is 10 U/mL, the amount of glucose isomerase is 10 U/mL, and the amount of glucokinase is 10 U/mL.

During the enzyme-catalyzed reaction, the temperature is 10-80° C., the pH is 5-9, and the reaction time is 1-120 hours. The preferred reaction temperature is 10-40° C., such as 10° C., 20° C., 30° C., 37° C. The preferred reaction pH is 6.5, 7.0, 7.5, 8.0. The preferred reaction time is 48-96 hours, such as 48 hours, 72 hours, 96 hours.

According to the present disclosure, allulose 6-phosphate 3-epimerase may be selected from the enzyme (KEGG No. b4085) encoded by the gene sequence SEQ ID No: 1 derived from *Escherichia coli*; specifically, the enzyme is EC: 5.1.3.

According to the present disclosure, allulose 6-phosphate phosphatase may be selected from the enzyme (KEGG No. b1727) encoded by the gene sequence SEQ ID No: 2 derived from *Escherichia coli*; specifically, the enzyme is EC: 3.1.3.23.

In the third aspect of the present disclosure, a method for preparing allulose or allose based on the coupling of enzymatic conversion and fermentation is provided, including enzymatic hydrolysis of a carbohydrate substrate with a multienzyme complex system, then preparation of a culture medium with the enzymatic hydrolysis solution as source of carbon, and fermentation with the recombinant strains as described in the first aspect of the present disclosure.

According to the present disclosure, the substrate is starch, a starch derivative or sucrose.

According to the present disclosure, the multienzyme complex system is any multienzyme complex described in the second aspect of the present disclosure; the recombinant strain may be any recombinant strain described in the first aspect of the present disclosure.

According to the present disclosure, the fermentation temperature is 30-37° C., and the fermentation time is 24-48 hours.

According to the present disclosure, the culture medium also contains a nitrogen source and sodium chloride; preferably, the nitrogen source is yeast powder or peptone.

In an embodiment of the present disclosure, a method for preparing allulose based on the coupling of enzymatic conversion and fermentation is provided. Firstly, the multienzyme reaction system as described in the second aspect of the present disclosure is used to convert starch or starch derivatives, for example, converting maltodextrin to allulose. The reaction solution obtained after the reaction is used as a carbon source to prepare a culture medium. After sterilization and centrifugation, the culture medium is fermented by using the above-described recombinant strain Allulose 5, and the residual glucose and fructose in the metabolic enzyme reaction system of the recombinant strain are converted to allulose.

In the multienzyme reaction system, the amounts of starch or starch derivatives and enzymes are the same as those in the second aspect of the present disclosure.

The fermentation medium of the recombinant strain Allulose5 contains the reaction solution after multienzymatic conversion as a carbon source, 1-40 g/L yeast powder as a nitrogen source and 1-10 g/L sodium chloride. Preferably, the amount of yeast powder is 10 g/L, the amount of sodium chloride is 10 g/L, the fermentation temperature is 30° C., and the fermentation time is 24-48 hours.

In an embodiment of the present disclosure, a method for preparing allose based on the coupling of enzymatic conversion and fermentation is provided. Firstly, the multienzyme reaction system as described in the second aspect of the present disclosure is used to convert starch or starch derivatives, for example, converting maltodextrin to allose. The obtained reaction solution after the reaction is used as a carbon source to prepare a culture medium. After sterilization and centrifugation, the culture medium is fermented by using the above-described recombinant strain Allose3, and the residual glucose and fructose in the metabolic enzyme reaction system of the recombinant strain are converted to allose.

In the reaction system, the amounts of starch or starch derivatives and enzymes are the same as those in the second aspect of the present disclosure. The fermentation medium of the recombinant strain Allose3 contains the reaction solution after multienzymatic conversion as a carbon source, 1-40 g/L yeast powder as a nitrogen source and 1-10 g/L sodium chloride. Preferably, the amount of yeast powder is 10 g/L, the amount of sodium chloride is 10 g/L, the fermentation temperature is 30° C., and the fermentation time is 24-48 hours.

In the present disclosure, when cells metabolize various carbon sources such as glucose, fructose, fructose 6-phosphate can be intracellularly synthesized. The latter can be converted to allulose 6-phosphate catalyzed by allulose 6-phosphate epimerase, and then allulose is synthesized by the dephosphorylation of allulose 6-phosphate. Meanwhile, allulose 6-phosphate can also be converted to allose 6-phosphate by aldose-ketose isomerization, and allose can be synthesized by the dephosphorylation of allose 6-phosphate. Therefore, the synthesis of allulose and allose can also be achieved by this route. The synthesis route involves the steps of phosphorylation and dephosphorylation and has the advantage of high conversion rate, compared with the traditional epimerization method. Thereby, the present disclosure proposes a new idea to construct microbially engineered strains by using genetic engineering technology and microbiological methods, and then to produce allulose and allulose derivatives using inexpensive substrates, such as glucose, fructose, starch, sucrose and molasses, by fermentation.

Beneficial Effects (1) In the present disclosure, recombinant engineered strains, which can highly express key enzyme genes in the process of fermentation of allulose and derivatives thereof, are constructed by analyzing glucose metabolic pathways of microorganisms, and a new path for large-scale production of allulose and derivatives thereof by fermentation is realized.

(2) Allulose and derivatives thereof are produced using the engineered strains constructed in the present disclosure, and the carbohydrate by-products produced in the metabolic process can be utilized as nutrients by microorganisms. Therefore, the recycling and reuse of carbohydrate compounds in the reaction process are realized, the conversion rates of raw materials are effectively improved, and the conversion rates of raw materials such as starch, sucrose and fructose syrup can reach 99% or more.

(3) When allulose and derivatives thereof are produced using the engineered strains constructed in the present disclosure, due to the metabolism of microorganisms and the regulation of expression levels of various intracellular enzymes in microorganisms, by-product residues in the final products are effectively suppressed, and single components of allulose, allose and allitol can be obtained. Thus, it effectively solves the problem of high cost of separating allose products in the traditional method.

(4) Allulose and allose are produced by an extracellular multienzyme cascade method in the present disclosure at low temperatures, and the reaction conditions are mild. The occurrence of Maillard reaction is reduced, and therefore the product qualities are improved.

Definition and Description of Terms

The terms "D-psicose", "allulose" and "psicose" are used interchangeably herein, and refer to an epimer of D-fructose at the C3 position, which belongs to a six-carbon rare ketose. The compound is shown as follows:

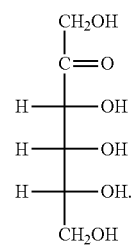

The term "derivative" refers to a compound made from a parent compound by substitution of H or other atoms/groups by other atoms or groups, or refers to a product obtained by isomerization or hydrolysis. As defined herein, the term "allulose derivative" includes, but is not limited to, allose and allitol. Among them, the terms "allose", "D-allose" and "Allose" are used interchangeably herein. The terms "D-allitol", "Allodulcitol", "Allitol" are used interchangeably herein. As used herein, the term "starch derivative" refers to monosaccharide, oligosaccharide or polysaccharide, which bears the same structural units as in starch, including but not limited to hydrolyzed starch, amylodextrine, maltodextrin, maltopolysaccharide or maltose. The term "starch" includes amylose and amylopectin.

The term "gene" is used broadly to refer to any segment of a nucleic acid molecule (typically DNA, but optionally RNA) encoding a polypeptide or expressed RNA. Thus, genes include sequences encoding expressed RNA (which can include polypeptide coding sequences or, for example, functional RNAs, such as ribosomal RNAs, tRNAs, antisense RNAs, microRNAs, short hairpin RNAs, ribozymes, etc.). Genes may further include regulatory sequences required for or affecting their expression, as well as sequences associated with the protein or RNA-coding sequence in its natural state, such as intron sequences, 5' or 3' untranslated sequences. In some examples, "gene" may only refer to a protein-coding portion of a DNA or RNA molecule, which may or may not include introns. A gene is preferably more than 50 nucleotides in length, more preferably more than 100 nucleotides in length, and can be, for example, between 50 nucleotides and 500,000 nucleotides in length, such as between 100 and 100,000 nucleotides in length, or between about 200 nucleotides and about 50,000 nucleotides in length, or between about 200 nucleotides and about 20,000 nucleotides in length. Genes can be obtained from a variety of sources, including cloning from a source of interest or synthesizing from known or predicted sequence information.

The term "wild-type" is used herein to refer to a nucleic acid sequence or an amino acid sequence that is naturally present in a host, or a host cell as it is naturally present in nature without artificial genetic modification or recombination. The terms "non-native" and "gene recombination" are used herein to refer to nucleic acid sequences or amino acid sequences that do not naturally occur in the host or are not constructed in such a way that they are naturally constructed in the host. The term "recombinant" or "engineered" is used herein to refer to a nucleic acid molecule that has been altered through human intervention. As non-limiting examples, a cDNA is a recombinant DNA molecule, such as any nucleic acid molecule that has been generated by in vitro polymerase reaction(s) or to which linkers have been attached, or that has been integrated into a vector (such as a cloning vector or expression vector).

When applied to organisms, the terms "transgenic" or "recombinant" or "engineered" or "genetically engineered" or "engineered strain" are used interchangeably herein to refer to organisms that have been manipulated by introduction of exogenous or recombinant nucleic acid sequences into the organisms. Generally, the heterologous polynucleotide is stably integrated within the genome such that the polynucleotide is passed on to successive generations. But the heterologous polynucleotide also can exist in an episome, and can be present in an artificial chromosome of transgenic organisms. The unnatural polynucleotide may be integrated into the genome alone or as part of a recombinant expression cassette. In other examples, a transgenic microorganism may include an introduced exogenous regulatory sequence operably linked to an endogenous gene of the transgenic microorganism. Non-limiting examples include gene knockouts, targeted mutations and gene replacement, promoter replacement, deletions or insertions, and introduction of transgenes into an organism. Recombinant or genetically engineered organisms can also be organisms into which constructs for gene "knockout" have been introduced. As used herein, "recombinant microorganism", "recombinant host cell" or "engineered strain" includes a progeny or a derivative of the recombinant microorganisms of the present disclosure.

The term "vector" refers to a nucleic acid molecule containing a selectable marker gene, or at least one of an origin of replication or an autonomously replicating sequence (ARS) that allows the vector to replicate in a host cell, and in some examples including both a selectable marker gene and at least one of an origin of replication or ARS. "Vector", "recombinant vector", "recombinant plasmid" in various examples contains single or combined expression sequences and/or may contain at least one sequence for mediating recombinations.

The genes introduced herein may be "derived from" a specified source, which include the isolation (in whole or in part) of a nucleic acid segment from the specified source, for example, by direct cloning, PCR amplification, or artificial synthesis from, or based on a sequence associated with the specified polynucleotide source, which may be, for example, a biological species. Genes or nucleic acid molecules or sequences (e.g., promoters) derived from a specific source or species also include those with sequence modification of the source nucleic acid molecules.

As used herein, the "ligation" of gene fragments or sequences refers to the functional joining of two or more sequences, so that an activity at one sequence or an activity of one sequence influences activities at other sequences or activities of other sequences. For example, an operable linkage between a target polynucleotide and a regulatory sequence (e.g., a promoter) is a functional link that allows the expression of the target polynucleotide. Furthermore, the "ligation" of gene fragments herein refers to positioning of a regulatory region and a coding sequence to be transcribed, so that the regulatory region is effective for regulating the transcription or translation of the target coding sequence.

EXAMPLES

Figure 1:
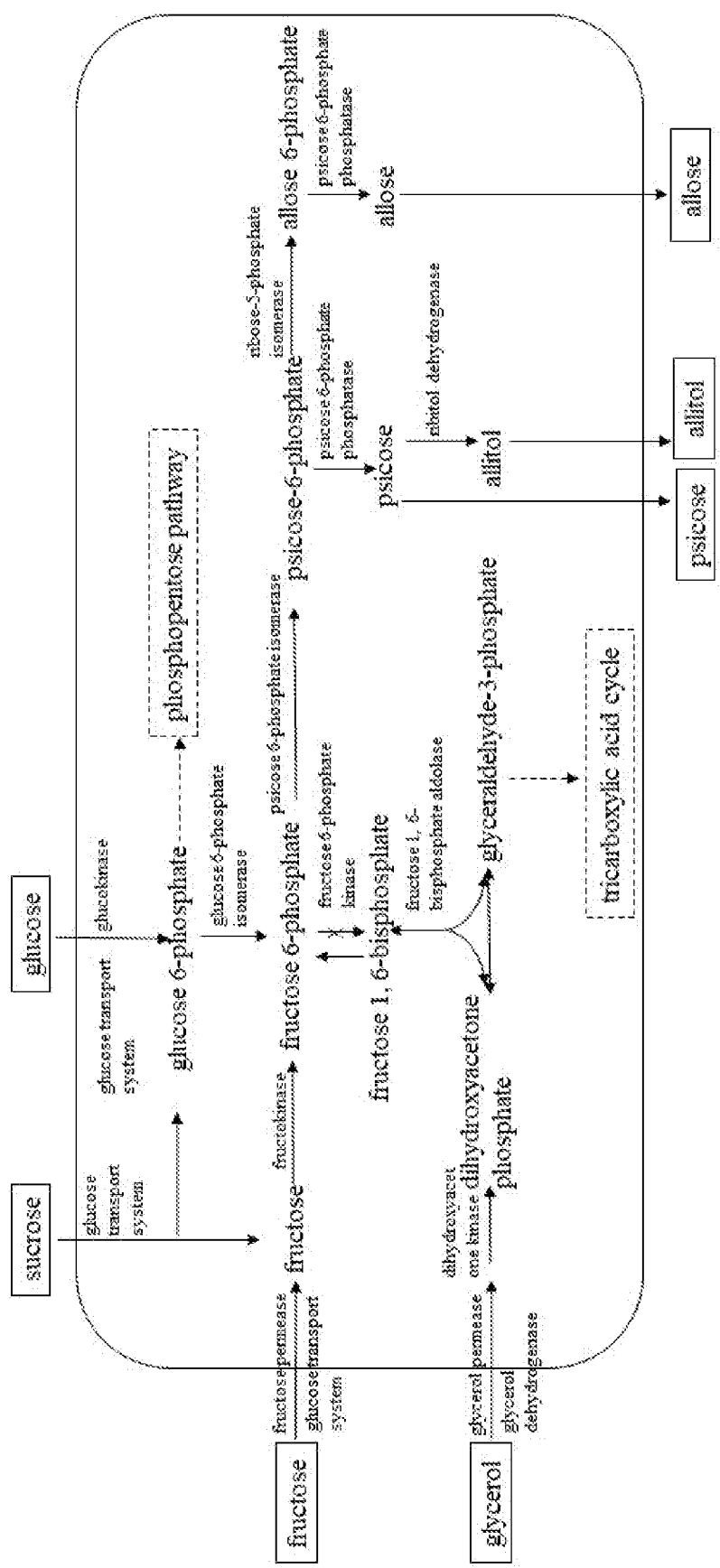
FIG. 1 is a flowchart illustrating a method for producing allulose and allulose derivatives in cells.

The present disclosure will be further illustrated in detail below in combination with the examples.

The percentage concentrations mentioned in the present disclosure and examples, unless otherwise specified, are the weight/weight percentage concentrations (W/W, in g/100 g), the weight/volume percentage concentrations (W/V, in g/100 mL), or the volume/volume percentage concentrations (V/V, in mL/100 mL).

The methods used in the following examples are all conventional methods unless otherwise specified. Specific steps can be seen in "Molecular Cloning: A Laboratory Manual" (Sambrook, J., Russell, David W., Molecular Cloning: A Laboratory Manual, 3rd edition, 2001, NY, Cold Spring Harbor).

Materials or reagents with the same names used in the examples are the same unless otherwise specified. The vectors pEC-XK99E (Kirchner O and Tauch A. 2003, Tools for genetic engineering in the amino acid-producing bacterium *Corynebacterium glutamicum*. J. Biotechnol. 104:287-299), pXMJ19 (Jakoby, M.; Ngouoto-Nkili, C.-E.; Burkovski, A. Construction and application of new *Corynebacterium glutamicum* vectors. Biotechnol. Tech. 1999, 13, 437-441), pK18mobsacB (Schäfer A, Tauch A, Jager W, Kalinowski J, Thierbach G, Puhler A. 1994. SmAllulose mobilizable multi-purpose cloning vectors derived from the *Escherichia coli* plasmids pK18 and pK19: selection of defined deletions in the chromosome of *Corynebacterium glutamicum*. Gene 145:69-73) used are those reported and published. Glucose, fructose, sucrose, brain heart infusion powder, sorbitol, yeast extract, peptone, maltodextrin, kanamycin, chloramphenicol and other drugs used are all purchased from Aladdin Reagent Co. Ltd. The primers used are synthesized by Jiangsu Jinweizhi Biotechnology Co., Ltd. Allulose, allose and allitol standards used are purchased from Sigma-Aldrich Co., Ltd. (China).

Accesses to obtain various biomaterials described in the examples are only for providing experiment materials acquisition, in order to satisfy specific disclosure, but should not be a limitation on the sources of the biomaterials when implementing the present disclosure. In fact, the sources of the used biomaterials are extensive, and any biomaterial that can be obtained without violating laws and moral ethics can be replaced based on indications in the examples.

The examples are implemented based on the technical solutions of the present disclosure, and the detailed embodiments and specific operation processes are given. The examples will aid in understanding the present disclosure, but the protection scope of the present disclosure is not limited to the following examples. It should be understood by those skilled in the art that modifications or substitutions in details and forms of the technical solutions of the present disclosure may be made without departing from the spirit and scope of the present disclosure, but these modifications or substitutions all fall within the protection scope of the present disclosure.

Example 1 Construction of Recombinant *Corynebacterium glutamicum* Strain Allulose1

1. Construction of Recombinant Expression Vector pEC-P6PE-P6PP

The allulose 6-phosphate 3-epimerase (P6PE) gene (SEQ ID No: 1) and the allulose 6-phosphate phosphatase (P6PP) gene (SEQ ID No: 2) derived from *Escherichia coli* according to the KEGG database were used to design Primer1, Primer2, Primer3 and Primer4. The corresponding sequences were obtained by PCR amplification. The gene P6PE and the expression vector pEC-XK99E (Kirchner O and Tauch A. 2003, tools for genetic engineering in the amino acid producing bacterium *Corynebacterium glutamicum*. J. biotechnology. 104:287-299) were digested with the restriction enzymes EcoRI and SmaI at the same time, and ligated together to obtain the recombinant plasmid pEC-P6PE. The gene P6PP and the expression vector pEC-P6PE were further digested with the restriction enzymes XbaI and PstI, and ligated together to obtain the recombinant expression vector pEC-P6PE-P6PP. The primer sequences are as follows:

```
Primer 1 SEQ ID NO: 15:
taccggaattcatgaaaatctccccctcgttaatg

Primer 2 SEQ ID NO: 16:
gatcccccgggttatgctgtttttgcatgaggct

Primer 3 SEQ ID NO: 17:
gatggtctagaaaaggaggacaaccatgtcaaccccgcgtcagattct

Primer 4 SEQ ID NO: 18:
gacaactgcagttaaccgagaaggtcttttgcggt
```

2. Obtaining Recombinant *Corynebacterium glutamicum* Strain Allulose1

The recombinant expression vector pEC-P6PE-P6PP was electroconverted into wild-type *Corynebacterium glutamicum* ATCC13032 to obtain recombinant strain Allulose1. The specific process is as follows:

2.1 Preparation of electrocompetent cells of *Corynebacterium glutamicum* ATCC13032 (100 OL), specifically including the following steps:
  (1) The strains were taken out at −80° C. and streak-inoculated in *Corynebacterium glutamicum*, and then placed at 30° C. for cultivation.
  (2) Single colonies were selected and dropped into a test tube containing 5 mL of brain heart infusion powder medium (51 g/L brain heart infusion powder, 91 g/L sorbitol), and cultured at 200 rpm and 30° C. overnight.
  (3) 1 mL of the above bacterial solution was taken and put into 100 mL of BHIS culture solution in a 500 mL shake flask, and cultured at 200 rpm and 30° C. The OD values were measured until an OD600 of 1.3-1.5 was reached. It took about 2-4 h.
  (4) Under sterile conditions, the bacterial solution was transferred to two 50 mL centrifuge tubes pre-cooled with ice. After balanced, the tubes were centrifuged for 20 min at 6000 rpm. The supernatants were discarded.
  (5) Cells were suspended in 10 mL of aqueous solution containing 10% (v/v) glycerol. The glycerol solutions were replenished to 20 mL, and centrifuged at 6000 rpm for 20 min after the tubes were balanced. The supernatants were discarded. Step (5) was repeated three times.
  (6) The tubes were inverted over filter papers to absorb the excess liquid. 1-mL 10% glycerol is added to the tubes to suspend the cells, and then the solution was transferred into another tubes.
  (7) The solutions were aliquoted in portions of 100 μl in 10 sterile aliquots, and stored at −80° C.

2.2 Conversion of the recombinant expression vector pEC-P6PE-P6PP into *Corynebacterium glutamicum* ATCC 13032, specifically including the following steps:
  (1) 2 mL brain heart infusion powder medium and 2 mL sorbitol were poured into a large sterile tube and heated in a 46° C. water bath.
  (2) The competent *Corynebacterium* glutamate cells were thawed on ice.
  (3) 8-12 μL plasmid was added to the competent cells (about 100 μL). The mixture was mixed by pipetting up and down, then sucked up and added to an electrode cup (previously stored in anhydrous ethanol, and dried on a filter paper before use). The electrode cup was given an electric shock of 1800V, and taken out quickly after the sound. The large pipette was adjusted to about 800 μL. The mixture was mixed with pre-warmed BHIS by pipetting up and down, then sucked up and added to a large sterile tube in a 46° C. water bath for 6 min.

(4) The sterile tube was placed in a shaker at 30° C. for 45-60 min.

(5) The sterile tube was placed in a centrifuge at 30° C. at 4200 rpm for 6 min.

(6) The bacterial solution was coated in a solid brain heart powder medium containing kanamycin (25 g/mL), and placed in an incubator at 30° C. for 36 hours.

2.3 The positive colonies growing on the kanamycin resistant plate were selected and verified by colony PCR using Primer1 and Primer4. 1381 BP DNA fragments obtained by PCR amplification were positive clones.

2.4 The correct strain confirmed by PCR was stored, which was the recombinant strain allulose1 containing allulose 6-phosphate 3-epimerase P6PE gene and allulose 6-phosphate phosphatase P6PP gene.

Example 2 Construction of Recombinant *Corynebacterium glutamicum* Strain Allulose3

1. Construction of Integrating Vector pK18mobsacB-Pfk'

The upstream sequences (SEQ ID No: 13) and downstream sequences (SEQ ID No: 14) of the fructose 6-phosphate kinase gene derived from *Corynebacterium glutamicum* according to the KEGG database were used to design Primer5, Primer6, Primer7 and Primer8. Primer5 and Primer6 were amplified by PCR to obtain the corresponding upstream sequences of pfk' gene. Primer7 and Primer8 were amplified by PCR to obtain the corresponding downstream sequences of pfk" gene. The fused PCR fragment pfk'-pfk" composed of the upstream and downstream sequences was obtained by fusion PCR. The fusion fragment of pfk'-pfk" and vector pK18mobsacB (Schäfer A, Tauch A, Jager W, Kalinowski J, Thierbach G, Puhler A. 1994. SmAllulose mobilizable multi-purpose cloning vectors derived from the *Escherichia coli* plasmids pK18 and pK19: selection of defined deletions in the chromosome of *Corynebacterium glutamicum*. Gene 145:69-73) were further digested with the restriction enzymes EcoRI and HindIII, and ligated together to obtain the recombinant plasmid pK18mobsacB-pfk. The specific primer sequences are as follows:

```
Primer 5 SEQ ID NO: 19:
accggaattcatgattttggtttccttctgcga

Primer 6 SEQ ID NO: 20:
ttcgaatggaacttccttcaagctggctgtgcggacgattcct

Primer 7 SEQ ID NO: 21:
aggaatcgtccgcacagccagcttgaaggaagttccattcgaacg

Primer 8 SEQ ID NO: 22:
actcaagcttgttaagacgcagctgaccagtg
```

2. Obtaining a Fructose 6-Phosphate Kinase Gene Knockout Recombinant Strain Allulose2

2.1 Electro-competent *Corynebacterium glutamicum* ATCC13032 cells were prepared, and the gene knockout vector pK18mobsacB-pfk was electroconverted into electrocompetent *Corynebacterium glutamicum* ATCC13032 cells.

2.2 The positive colonies growing on a kanamycin resistant plate were selected, and streaked on a LB plate containing 10% sucrose, cultured for 24 h at 30° C. The purpose of this step is to screen kanamycin deletion clones based on sucrose-induced lethality.

2.3 Several colonies were selected from the LB sucrose plate, and verified by colony PCR using Primer5 and Primer8. 1822 DNA fragments obtained by PCR amplification were positive clones.

2.4 The correct strain confirmed by PCR was stored, which was the recombinant *Corynebacterium glutamicum* strain without fructose 6-phosphate kinase activity, named as Allulose2.

3. Obtaining Recombinant *Corynebacterium glutamicum* Strain Allulose3

The recombinant expression vector pEC-P6PE-P6PP bearing the allulose 6-phosphate 3-epimerase and allulose 6-phosphate phosphatase genes were electroconverted into the recombinant strain Allulose2 to obtain a recombinant strain Allulose3. The specific process refers to the process of electrotransformation in Example 1.

Example 3 Construction of Recombinant *Corynebacterium glutamicum* Strain Allulose4

1. Construction of Recombinant Expression Vector pXMJ19-GlK-PGI

The glucokinase gene Glk (SEQ ID No: 4) and glucose 6-phosphate isomerase gene PGI (SEQ ID No: 5) derived from *Corynebacterium glutamicum* according to the KEGG database were used to design Primer9, Primer10, Primer11 and Primer12. The glucokinase gene Glk and glucose 6-phosphate isomerase gene PGI were amplified by PCR using *Corynebacterium glutamicum* genome as a template. The gene PGI and the expression vector pXMJ19 (Jakoby, M.; Ngouoto-Nkili, C.-E.; Burkovski, A. Construction and application of new *Corynebacterium glutamicum* vectors. Biotechnol. Tech. 1999, 13, 437-441) were digested with the restriction enzymes HindIII and PstI at the same time, and ligated together using T4 ligase to obtain the expression vector pXMJ19-PGI. The gene Glk and the expression vector pXMJ19-PGI were further digested with the restriction enzymes PstI and XbaI at the same time to obtain the recombinant expression vector pXMJ19-GIK-PGI. The specific primer sequences are as follows:

```
Primer 9 SEQ ID NO: 23:
cactcaagcttatgggatccatggcggacatttcgaccac

Primer 10 SEQ ID NO: 24:
gacaactgcagctacctatttgcgcggtaccact

Primer 11 SEQ ID NO: 25:
gacaactgcagaaaggaggacaaccatgccacaaaaaccggccagtt

Primer 12 SEQ ID NO: 26:
gatggtctagattagttggcttccactacagagc
```

2. Obtaining a Recombinant *Corynebacterium glutamicum* Strain Allulose4

The recombinant expression vector pXMJ19-GIK-PGI was electroconverted into the recombinant strain Allulose3 to obtain a recombinant strain Allulose4. The specific process refers to the process of electrotransformation in Example 1.

Example 4 Construction of Recombinant *Corynebacterium glutamicum* Strain Allulose5

1. Construction of Recombinant Expression Vector pEC-P6PE-P6PP-FK-GIF

Nucleotide sequence of a tuf promoter derived from *Corynebacterium glutamicum*, the fructose permease gene Glf (SEQ ID NO:6) derived from *Zymomonas mobilis*, and the fructokinase gene Frk (SEQ ID NO:7) derived from *Enterococcus faecalis* according to the NCBI database were used to design Primer13, Primer14, Primer15, Primer16, Primer17 and Primer18. Fragments of the tuf promoter, the fructose permease gene Glf and the fructokinase gene Frk were obtained by PCR amplification. The fusion fragment of tuf-glf-frk was obtained by using the fusion PCR strategy and using the above three fragments as a template, and constructed into the recombinant expression plasmid pEC-P6PE-P6PP by enzyme digestion and ligation to obtain the recombinant expression plasmid pEC-P6PE-P6PP-FK-GLF.

```
Primer13 SEQ ID NO: 27:
gatggtctagatggccgttaccctgcgaatgt

Primer14 SEQ ID NO: 28:
agtacccagattttccattcattgtatgtcctcctggacttcgtg

Primer15 SEQ ID NO: 29:
cacgaagtccaggaggacatacaatgaatggaaaaatctgggtact

Primer16 SEQ ID NO: 30:
accctgactactttcagaactcattcacagcgagcgctgaagatcgt

Primer17 SEQ ID NO: 31:
acgatcttcagcgctcgctgtgaaaaggaggacaaccatgagttctgaa
agtagtcagggt Primer18 SEQ ID NO: 32:
ctacttctgggagcgccacatctcct
```

2. Obtaining a Recombinant *Corynebacterium glutamicum* Strain Allulose5

The recombinant expression vector pEC-P6PE-P6PP-FK-GIF were electroconverted into the fructose 6-phosphate kinase gene knockout Allulose2 to obtain a recombinant strain Allulose5. The specific process refers to the process of electrotransformation in Example 1.

Example 5 Construction of Recombinant *Corynebacterium glutamicum* Strain Allulose6

1. Construction of Recombinant Expression Vector pXMJ19-GlK-PGI-GlpF-DhaD-DhaK

Nucleotide sequence of a tuf promoter derived from *Corynebacterium glutamicum*, the glycerol permease gene GlpF (SEQ ID NO:8) derived from *Escherichia coli*, and the glycerol dehydrogenase gene DhaD (SEQ ID NO:9) derived from *Klebsiella pneumoniae*, and the dihydroxyacetone kinase gene DhaK (SEQ ID NO:10) according to the NCBI database were used to design Primer19, Primer20, Primer21, Primer22, Primer23 and Primer24. The RBS site sequence (AAAGGAGGACAACC) was included in Primer21 and Primer23, and the SmaI and XbaI digestion sites were included in Primer19 and Primer24. The specific primer sequences are as follows:

```
Primer19 SEQ ID NO: 33:
gatggtctagaaaaggaggacaaccatgagtcaaacatcaaccttgaaa
g

Primer20 SEQ ID NO: 34:
gagattgaataacttttagcatatctatatctccttattacagcgaagc
ttttgt Primer21 SEQ ID NO: 35:
acaaaaagcttcgctgtaataaggagatatagatatgctaaaagttatt
caatctc Primer22 SEQ ID NO: 36:
tggttaaaaaagaattgagacatggttgtcctccttttaacgcgccag
ccactgctgtc Primer23 SEQ ID NO: 37:
gacagcagtggctggcgcgttaaaaaggaggacaaccatgtctcaattc
ttttttaacca Primer24 SEQ ID NO: 38:
tcccccgggtctagattagcccagctcactctccgc
```

Using *Escherichia coli* MG1655 genomic DNA as a template, the glycerol permease gene was amplified by PCR using Primer19 and Primer20, the glycerol dehydrogenase gene was amplified by PCR using Primer21 and Primer22, and the dihydroxyacetone kinase gene was amplified by PCR using Primer23 and Primer24. The fusion fragment of glpF-rhaD-yqaB was obtained by using the fusion PCR method. The fusion gene fragment and vector pXMJ19-GIK-PGI were digested with the restriction enzymes SmaI and XbaI at the same time, and ligated together using T4 ligase to obtain the recombinant plasmid pXMJ19-GlK-PGI-glpF-DhaD-DhaK.

2. Obtaining a Recombinant *Corynebacterium glutamicum* Strain Allulose6

The recombinant expression vector pXMJ19-GlK-PGI-GlpF-DhaD-DhaK and pEC-P6PE-P6PP-FK-GIF were electroconverted into the recombinant strain Allulose2 at the same time to obtain a recombinant strain Allulose6. The specific process refers to the process of electrotransformation in Example 1.

Example 6 Use of Recombinant *Corynebacterium glutamicum* Strains Allulose1, Allulose3 and Allulose4 in Producing Allulose A1. Recombinant *Corynebacterium glutamicum* Strain Allulose1 Used to Ferment Glucose to Synthesize Allulose 100 mL BHI medium (brain heart infusion powder 37 g/L, kanamycin 25 ng/ml) was selected. A final concentration of 2% glucose (weight/volume (w/v, unit g/100 mL) percentage concentration) was added. The recombinant *Corynebacterium glutamicum* strain Allulose1 was cultured at 30° C. and 200 rmp for 12-24 h. and the inoculation amount of the strain was 2%. After fermentation, the sample was centrifuged at 14000 rmp for 20 min and filtered with a 0.22 μm microporous membrane. The filtrate was analyzed by HPLC. HPLC analysis was performed under the following conditions: the instrument was Agilent HPLC 1200, the analytical column was Sugar-Pak, the mobile phase was ultrapure water, the flow rate was 0.4 mL/min, the column temperature was 80° C., the detector was differential refraction index detector, and the sample volume was 10 □L.

A2. Recombinant *Corynebacterium glutamicum* Strain Allulose3 Used to Ferment Glucose to Synthesize Allulose The cultivation method of recombinant strain Allulose3 was the same as that of A1 in the example. A final concentration of 2% glucose (weight/volume (w/v, unit g/100 mL) percentage concentration) was added to the culture medium. The inoculation amount of the strain was 2%. The sample was cultured for 24-48 h. The final sample after fermentation was detected by HPLC.

A3. Recombinant *Corynebacterium glutamicum* Strain Allulose4 Used to Ferment Glucose to Synthesize Allulose The cultivation method of recombinant strain Allulose4 was the same as that of A1 in the example. A final concentration of 2% glucose (weight/volume (w/v, unit g/100 mL) percentage concentration) was added to the culture medium.

The inoculation amount of the strain was 2%. The sample was cultured for 24-48 h. The final sample after fermentation was detected by HPLC.

Figure 2:
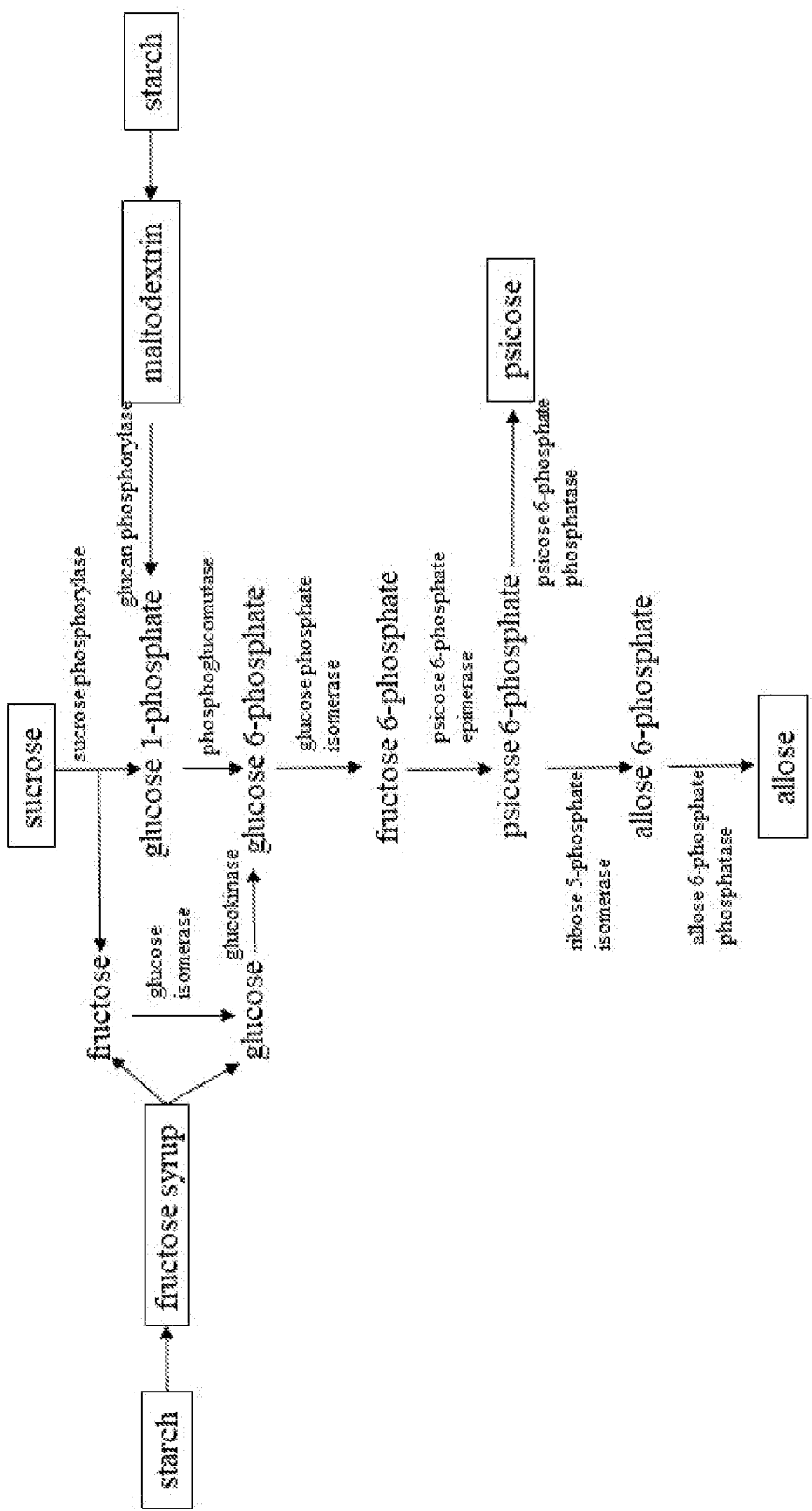
FIG. 2 is a flowchart illustrating a method for producing allulose and allulose derivatives by extracellular enzyme catalysis.

The results of fermentation showed that after 48 hours, the recombinant strain Allulose1 could ferment glucose to synthesize 1.8 g/L allulose. The recombinant strain Allulose3 could ferment glucose to synthesize 10.6 g/L allulose, and compared with the recombinant strain Allulose1, the yield of allulose increased nearly 6 times. The recombinant strain Allulose4 could ferment glucose to synthesize 14.8 g/L allulose, and compared with the recombinant strain Allulose3, the yield of allulose increased nearly 30%. The results are shown in FIG. 2 ((a) for the fermentation broth at 0 h, (b) for the fermentation broth at 48 h, and (c) for pure allulose).

Example 7 Use of Recombinant *Corynebacterium glutamicum* Strain Allulose5 in Producing Allulose 1. Recombinant *Corynebacterium glutamicum* Strain Allulose5 Used to Ferment Glucose to Synthesize Allulose The cultivation method of recombinant strain Allulose5 was the same as that of A1 in Example 6. A final concentration of 2% glucose (weight/volume (w/v, unit g/100 mL) percentage concentration) was added to the culture medium. The inoculation amount of the strain was 2%. The sample was cultured for 48 h. The final sample after fermentation was detected by HPLC.

2. Recombinant *Corynebacterium glutamicum* Strain Allulose5 Used to Ferment Fructose to Synthesize Allulose The cultivation method of recombinant strain Allulose5 was the same as that of recombinant strain Allulose1 in Example 6. A final concentration of 2% fructose (weight/volume (w/v, unit g/100 mL) percentage concentration) was added to the culture medium. The inoculation amount of the strain was 2%. The sample was cultured for 48 h. The final sample after fermentation was detected by HPLC.

3. Recombinant *Corynebacterium glutamicum* Strain Allulose5 Used to Ferment Sucrose to Synthesize Allulose The cultivation method of recombinant strain Allulose5 was the same as that of recombinant strain Allulose1 in Example 6. A final concentration of 2% sucrose (weight/volume (w/v, unit g/100 mL) percentage concentration) was added to the culture medium. The inoculation amount of the strain was 2%. The sample was cultured for 48 h. The final sample after fermentation was detected by HPLC.

Figure 3:
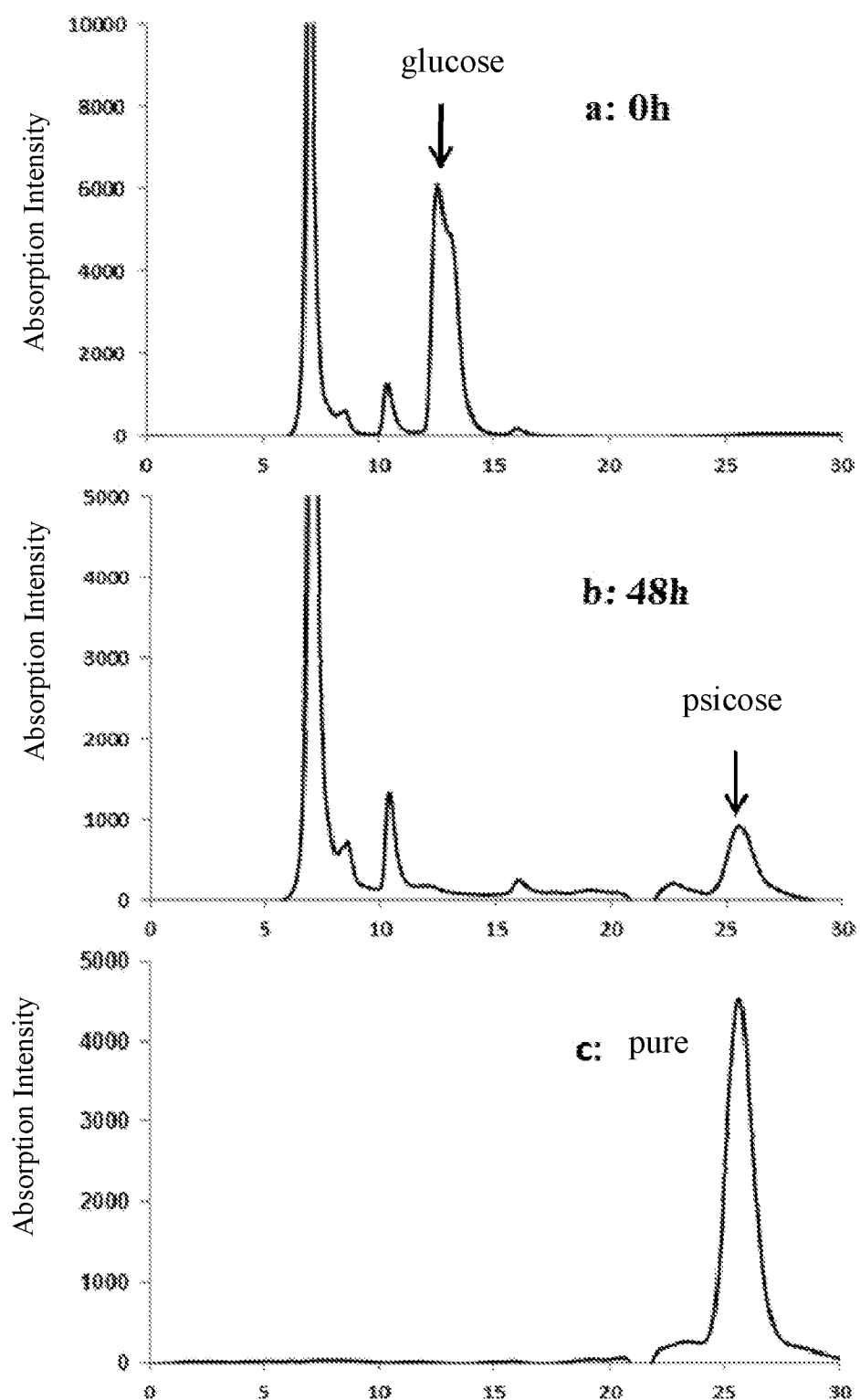
FIG. 3 depicts the results of HPLC analysis of the synthesis of allulose by fermenting glucose with recombinant strain Allulose4 in Example 6.

The results of fermentation showed that after 48 hours, the recombinant strain Allulose5 could ferment glucose to synthesize 12.8 g/L allulose, ferment fructose to synthesize 13.6 g/L allulose, and ferment sucrose to synthesize 11.6 g/L allulose. The results are shown in FIG. 3 ((a) for the fermentation broth at 0 h, (b) for the fermentation broth at 48 h, and (c) for pure allulose).

Example 8 Use of Recombinant *Corynebacterium glutamicum* Strain Allulose6 in Producing Allulose 1. Recombinant *Corynebacterium glutamicum* Strain Allulose6 Used to Ferment Glucose to Synthesize Allulose The cultivation method of recombinant strain Allulose6 was the same as that of recombinant strain Allulose1 in Example 6. A final concentration of 2% sucrose (weight/volume (w/v, unit g/100 mL) percentage concentration) was added to the culture medium. The inoculation amount of the strain was 2%. The sample was cultured for 48 h. The final sample after fermentation was detected by HPLC.

2. Recombinant *Corynebacterium glutamicum* Strain Allulose6 Used to Ferment Fructose to Synthesize Allulose The cultivation method of recombinant strain Allulose6 was the same as that of recombinant strain Allulose1 in Example 6. A final concentration of 2% fructose (weight/volume (w/v, unit g/100 mL) percentage concentration) was added to the culture medium. The inoculation amount of the strain was 2%. The sample was cultured for 48 h. The final sample after fermentation was detected by HPLC.

3. Recombinant *Corynebacterium glutamicum* Strain Allulose6 Used to Ferment Sucrose to Synthesize Allulose The cultivation method of recombinant strain Allulose6 was the same as that of recombinant strain Allulose1 in Example 6. A final concentration of 2% sucrose (weight/volume (w/v, unit g/100 mL) percentage concentration) was added to the culture medium. The inoculation amount of the strain was 2%. The sample was cultured for 48 h. The final sample after fermentation was detected by HPLC.

4. Recombinant *Corynebacterium glutamicum* Strain Allulose6 Used to Ferment Glycerol to Synthesize Allulose The cultivation method of recombinant strain Allulose6 was the same as that of recombinant strain Allulose1 in Example 6. A final concentration of 2% glycerol (weight/volume (w/v, unit g/100 mL) percentage concentration) was added to the culture medium. The inoculation amount of the strain was 2%. The sample was cultured for 48 h. The final sample after fermentation was detected by HPLC.

Figure 4:
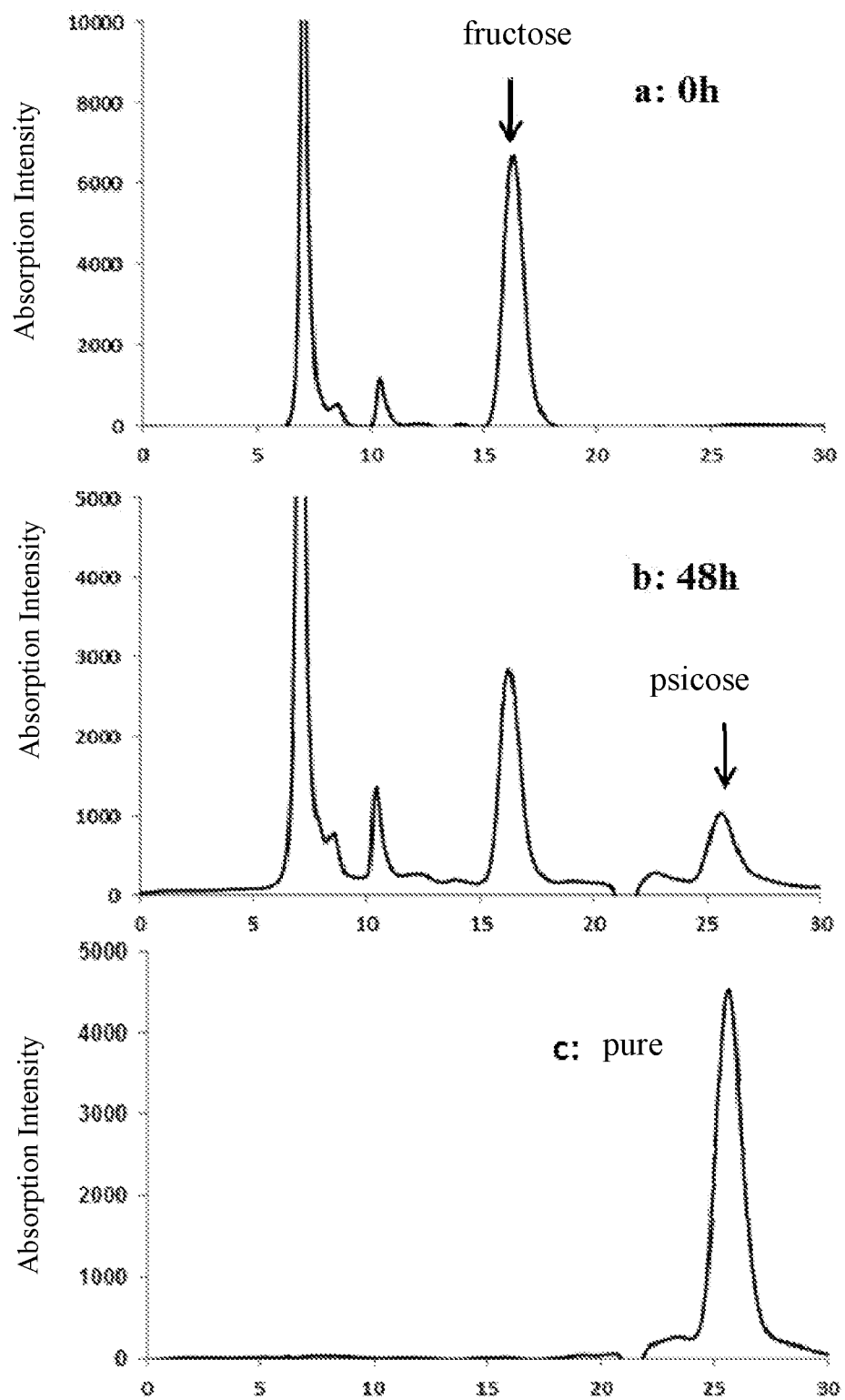
FIG. 4 depicts the results of HPLC analysis of the synthesis of allulose by fermenting fructose with recombinant strain Allulose5 in Example 7.
Figure 5:
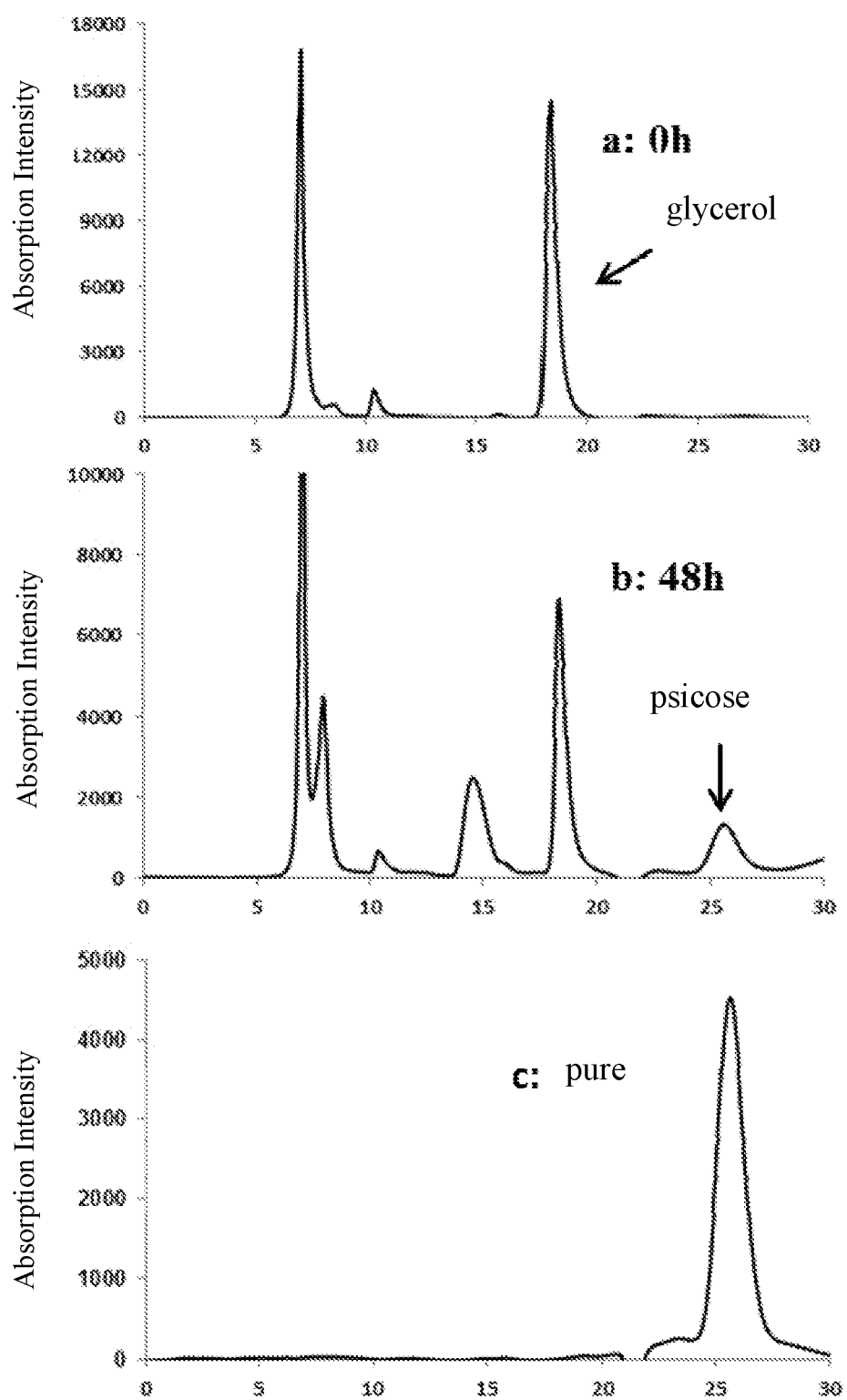
FIG. 5 depicts the results of HPLC analysis of the synthesis of allulose by fermenting glycerol with recombinant strain Allulose6 in Example 8.

The results of fermentation showed that after 48 hours, the recombinant strain Allulose6 could ferment glucose to synthesize 12.1 g/L allulose, ferment fructose to synthesize 12.6 g/L allulose, ferment sucrose to synthesize 10.8 g/L allulose, and ferment glycerol to synthesize 3.4 g/L allulose. The results are shown in FIG. 4 ((a) for the fermentation broth at 0 h, (b) for the fermentation broth at 48 h, and (c) for pure allulose).

Example 9 Construction of Recombinant *Corynebacterium glutamicum* Strains Allose1, Allose2, Allose3 and Allose4

1. Construction of Recombinant Expression Vector pEC-P6PE-RpiB-P6PP

The allulose 6-phosphate 3-epimerase (P6PE) gene (SEQ ID No: 1), the allulose 6-phosphate phosphatase (P6PP) gene (SEQ ID No: 2), and the ribose-5-phosphate isomerase (RpiB) gene (SEQ ID No: 11) derived from *Escherichia coli* according to the KEGG database were used to design Primer25, Primer26, Primer27, Primer28, Primer29 and Primer30. The corresponding sequences were obtained by PCR amplification. The fusion fragment of P6PE-RpiB-P6PP consisting of the genes P6PE, RpiB and P6PP was obtained by using the fusion PCR method. The fusion fragment and the expression vector pEC-XK99E were digested with the restriction enzymes EcoRI and PstI at the same time, and ligated together to obtain the recombinant plasmid pEC-P6PE-RpiB-P6PP. The primer sequences are as follows:

```
Primer25 SEQ ID NO: 39:
taccggaattcatgaaaatctccccctcgttaatg

Primer26 SEQ ID NO: 40:
gaatctgacgcggggttgacatggttgtcctcctttttatgctgttttt
gcatgag Primer27 SEQ ID NO: 41:
ctcatgcaaaaacagcataaaaaggaggacaaccatgtcaacccgcgt
cagattc
```

-continued
```
Primer28 SEQ ID NO: 42:
atcacagccaaatgcaatcttttcatggttgtcctccttttaaccga
gaaggtcttttg Primer29 SEQ ID NO: 43:
caaaagaccttctcggttaaaaaggaggacaaccatgaaaaagattgca
tttggctgtgat Primer30 SEQ ID NO: 44:
gacaactgcagttaaccgagaaggtcttttgcggt
```

2. Obtaining a Recombinant *Corynebacterium glutamicum* Strain Allose1

The recombinant expression vector pEC-P6PE-RpiB-P6PP bearing the allulose 6-phosphate 3-epimerase, allulose 6-phosphate phosphatase and ribose-5-phosphate isomerase genes were electroconverted into wild-type *Corynebacterium glutamicum* ATCC13032 to obtain a recombinant strain Allose1.

3. Obtaining a Recombinant *Corynebacterium glutamicum* Strain Allose2

The recombinant expression vector pEC-P6PE-RpiB-P6PP bearing the allulose 6-phosphate 3-epimerase, allulose 6-phosphate phosphatase and ribose-5-phosphate isomerase genes were electroconverted into the fructose 6-phosphate kinase gene knockout strain Allulose2 to obtain a recombinant strain Allose2.

4. Obtaining a Recombinant *Corynebacterium glutamicum* Strain Allose3

The recombinant expression vector pEC-P6PE-RpiB-P6PP bearing the allulose 6-phosphate 3-epimerase, allulose 6-phosphate phosphatase and ribose-5-phosphate isomerase genes and the expression vector pXMJ19-GlK-PGI bearing the glucokinase (Glk) and glucose 6-phosphate isomerase (PGI) genes were converted into the fructose 6-phosphate kinase gene knockout strain Allulose2 to obtain a recombinant strain Allose3.

5. Obtaining a Recombinant *Corynebacterium glutamicum* Strain Allose4

The recombinant expression vector pEC-P6PE-RpiB-P6PP bearing the allulose 6-phosphate 3-epimerase, allulose 6-phosphate phosphatase and ribose-5-phosphate isomerase genes and the expression vector pXMJ19-GlK-PGI-GlpF-DhaD-DhaK bearing the glucokinase (Glk), glucose 6-phosphate isomerase (PGI), glycerol permease (GlpF), glycerol dehydrogenase (DhaD) and dihydroxyacetone kinase Dhak (DhaK) genes were converted into the fructose 6-phosphate kinase gene knockout strain Allulose2 described in example 2 to obtain a recombinant strain Allose4.

Example 10 Use of Recombinant *Corynebacterium glutamicum* Strains Allose1, Allose2, Allose3 and Allose4 in Producing Allose 1. Recombinant *Corynebacterium glutamicum* Strain Allose1 Used to Ferment Glucose to Synthesize Allose The cultivation method of recombinant strain Allose1 was the same as that of recombinant strain Allulose1 in Example 6. A final concentration of 2% glucose (weight/volume (w/v, unit g/100 mL) percentage concentration) was added to the culture medium. The inoculation amount of the strain was 2%. The sample was cultured for 48 h. The final sample after fermentation was detected by HPLC.

2. Recombinant *Corynebacterium glutamicum* Strain Allose2 Used to Ferment Glucose to Synthesize Allose The cultivation method of recombinant strain Allose2 was the same as that of recombinant strain Allulose1 in Example 6. A final concentration of 2% glucose (weight/volume (w/v, unit g/100 mL) percentage concentration) was added to the culture medium. The inoculation amount of the strain was 2%. The sample was cultured for 48 h. The final sample after fermentation was detected by HPLC.

3. Recombinant *Corynebacterium glutamicum* Strain Allose3 Used to Ferment Glucose to Synthesize Allose The cultivation method of recombinant strain Allose3 was the same as that of recombinant strain Allulose1 in Example 6. A final concentration of 2% glucose (weight/volume (w/v, unit g/100 mL) percentage concentration) was added to the culture medium. The inoculation amount of the strain was 2%. The sample was cultured for 48 h. The final sample after fermentation was detected by HPLC.

4. Recombinant *Corynebacterium glutamicum* Strain Allose4 Used to Ferment Glycerol to Synthesize Allose The cultivation method of recombinant strain Allose4 was the same as that of recombinant strain Allulose1 in Example 6. A final concentration of 2% glycerol (weight/volume (w/v, unit g/100 mL) percentage concentration) was added to the culture medium. The inoculation amount of the strain was 2%. The sample was cultured for 48 h. The final sample after fermentation was detected by HPLC.

The results of fermentation showed that after 48 hours, the recombinant strain Allose1 could ferment glucose to synthesize 1.0 g/L allose, the recombinant strain Allose2 could ferment glucose to synthesize 7.6 g/L allose. Comparing with the recombinant strain Allose1, the allose yield of Allose2 increased nearly 7.6 times. The recombinant strain Allose3 could ferment glucose to synthesize 9.2 g/L allose, and compared with the recombinant strain Allose2, the yield of allose increased nearly 26.3%. The recombinant strain Allose4 could ferment glycerol to synthesize 2.8 g/L allose.

Example 11 Construction of Recombinant *Corynebacterium glutamicum* Strains Allitol1, Allitol2, Allitol3 and Allitol4

1. Construction of Recombinant Expression Vector pEC-P6PE-P6PP-RDH

The allulose 6-phosphate 3-epimerase (P6PE) gene (SEQ ID No: 1), the allulose 6-phosphate phosphatase (P6PP) gene (SEQ ID No: 2), and the ribitol dehydrogenase (RDH) gene (SEQ ID No: 12) derived from *Escherichia coli* according to the KEGG database were used to design Primer31, Primer32, Primer33, Primer34, Primer35 and Primer36. The corresponding sequences were obtained by PCR amplification. The fusion fragment of P6PE-P6PP-RDH consisting of the genes P6PE, P6PP and RDH was obtained by using the fusion PCR method. The fusion fragment and the expression vector pEC-XK99E were digested with the restriction enzymes EcoRI and PstI at the same time, and ligated together to obtain the recombinant plasmid pEC-P6PE-P6PP-RDH. The primer sequences are as follows:

```
Primer31 SEQ ID NO: 45:
taccggaattcatgaaaatctccccctcgttaatg

Primer32 SEQ ID NO: 46:
gaatctgacgcggggttgacatggttgtcctccttttatgctgttttt
gcatgag Primer33 SEQ ID NO: 47:
ctcatgcaaaaacagcataaaaggaggacaaccatgaaaaagattgca
tttggctgtgat
```

```
-continued
Primer34 SEQ ID NO: 48:
caaaagaccttctcggttaaggttgtcctccttttttaaccgagaaggtc
ttttg Primer35 SEQ ID NO: 49:
ccaaatgcaatcttttccataaaggaggacaaccatgaaccactctgtc
tcctctat Primer36 SEQ ID NO: 50:
gacaactgcagtcagagatccacgctgttcggc
```

2. Obtaining a Recombinant *Corynebacterium glutamicum* Strain Allitol1

The recombinant expression vector pEC-P6PE-P6PP-RDH bearing the allulose 6-phosphate 3-epimerase, allulose 6-phosphate phosphatase and ribitol dehydrogenase (RDH) genes were electroconverted into wild-type *Corynebacterium glutamicum* ATCC13032 to obtain a recombinant strain Allitol 1.

3. Obtaining a Recombinant *Corynebacterium glutamicum* Strain Allitol2

The recombinant expression vector pEC-P6PE-P6PP-RDH bearing the allulose 6-phosphate 3-epimerase, allulose 6-phosphate phosphatase and ribitol dehydrogenase (RDH) genes were electroconverted into the fructose 6-phosphate kinase gene knockout strain Allulose2 to obtain a recombinant strain Allitol2.

4. Obtaining a Recombinant *Corynebacterium glutamicum* Strain Allitol3

The recombinant expression vector pEC-P6PE-P6PP-RDH bearing the allulose 6-phosphate 3-epimerase, allulose 6-phosphate phosphatase and ribitol dehydrogenase (RDH) genes and the expression vector pXMJ19-GlK-PGI bearing the glucokinase (Glk) and glucose 6-phosphate isomerase (PGI) genes were converted into the fructose 6-phosphate kinase gene knockout strain Allulose2 to obtain a recombinant strain Allitol3.

5. Obtaining a Recombinant *Corynebacterium glutamicum* Strain Allitol4

The recombinant expression vector pEC-P6PE-P6PP-RDH bearing the allulose 6-phosphate 3-epimerase, allulose 6-phosphate phosphatase and ribitol dehydrogenase (RDH) genes and the expression vector pXMJ19-GlK-PGI-GlpF-DhaD-DhaK bearing the glucokinase (Glk), glucose 6-phosphate isomerase (PGI), glycerol permease (GlpF), glycerol dehydrogenase (DhaD) and dihydroxyacetone kinase Dhak (DhaK) genes were converted into the fructose 6-phosphate kinase gene knockout strain Allulose2 to obtain a recombinant strain Allitol4.

Example 12 Use of Recombinant *Corynebacterium glutamicum* Strains Allitol1, Allitol2, Allitol3 and Allitol4 in Producing Allitol 1. Recombinant *Corynebacterium glutamicum* Strain Allitol1 Used to Ferment Glucose to Synthesize Allitol The cultivation method of recombinant strain Allitol1 was the same as that of recombinant strain Allulose1 in Example 6. A final concentration of 2% glucose (weight/volume (w/v, unit g/100 mL) percentage concentration) was added to the culture medium. The inoculation amount of the strain was 2%. The sample was cultured for 48 h. The final sample after fermentation was detected by HPLC.

2. Recombinant *Corynebacterium glutamicum* Strain Allitol2 Used to Ferment Glucose to Synthesize Allitol The cultivation method of recombinant strain Allitol2 was the same as that of recombinant strain Allulose1 in Example 6. A final concentration of 2% glucose (weight/volume (w/v, unit g/100 mL) percentage concentration) was added to the culture medium. The inoculation amount of the strain was 2%. The sample was cultured for 48 h. The final sample after fermentation was detected by HPLC.

3. Recombinant *Corynebacterium glutamicum* Strain Allitol3 Used to Ferment Glucose to Synthesize Allitol The cultivation method of recombinant strain Allitol3 was the same as that of recombinant strain Allulose1 in Example 6. A final concentration of 2% glucose (weight/volume (w/v, unit g/100 mL) percentage concentration) was added to the culture medium. The inoculation amount of the strain was 2%. The sample was cultured for 48 h. The final sample after fermentation was detected by HPLC.

4. Recombinant *Corynebacterium glutamicum* Strain Allitol4 Used to Ferment Glycerol to Synthesize Allitol The cultivation method of recombinant strain Allitol4 was the same as that of recombinant strain Allulose1 in Example 6. A final concentration of 2% glycerol (weight/volume (w/v, unit g/100 mL) percentage concentration) was added to the culture medium. The inoculation amount of the strain was 2%. The sample was cultured for 48 h. The final sample after fermentation was detected by HPLC.

The results of fermentation showed that after 48 hours, the recombinant strain Allitol1 could ferment glucose to synthesize 0.6 g/L allitol, the recombinant strain Allitol2 could ferment glucose to synthesize 5.3 g/L allitol, the recombinant strain Allitol3 could ferment glucose to synthesize 7.4 g/L allitol and compared with the recombinant strain Allitol2, the yield of allitol increased nearly 7.4 times. The recombinant strain Allitol4 could ferment glycerol to synthesize 2.1 g/L allitol.

Example 13 Conversion of Maltodextrin to Allulose by Extracellular Multienzyme Catalysis To establish an extracellular multienzyme system for converting maltodextrin into allulose. The key enzymes include: (1) glucan phosphorylase (EC: 2.4.1.1), which catalyzes the conversion of glucan to glucose 1-phosphate, (2) phosphoglucomutase (EC: 5.4.2.2), which catalyzes the conversion of glucose 1-phosphate to glucose 6-phosphate; (3) glucose phosphate isomerase (EC: 5.3.1.9), which catalyzes the conversion of glucose 6-phosphate to fructose 6-phosphate; (4) allulose 6-phosphate 3-epimerase (EC: 5.1.3.-), which catalyzes the conversion of fructose 6-phosphate to allulose 6-phosphate; (5) allulose 6-phosphate phosphatase, which catalyzes the dephosphorylation of allulose 6-phosphate to allulose; (6) isoamylase AI, which catalyzes maltodextrin to be a linear glycan; (7) glucan transferase (GT), which catalyzes the polymerization of maltose to produce maltotetraose or oligosaccharides with higher degree of polymerization.

In the present disclosure, glucan phosphorylase was derived from *Thermotoga maritima* and the gene number on KEGG is TM1168; phosphoglucomutase was derived from *Thermotoga maritima* and the gene number on KEGG is TM0769; glucose phosphate isomerase was derived from *Clostridium thermocellum* and the gene number on KEGG is Cthe0217; allulose 6-phosphate 3-epimerase was derived from *Escherichia coli* and the gene number on KEGG is b4085 (SEQ ID NO: 1); allulose 6-phosphate phosphatase was derived from *Escherichia coli* and the gene number on KEGG is b1727 (SEQ ID NO:2); isoamylase was derived from *Sulfolobus tokodaii* and the gene number on KEGG is ST0928; glucan transferase was derived from *Thermococcus litoralis*, and the gene number on KEGG is OCC_10078. These genomic DNAs are available from ATCC official website (www.atcc.org). The seven genes were obtained from the corresponding genomic DNA by PCR using different primers and cloned into the pET21 vector by enzyme digestion and ligation, to obtain corresponding expression vectors: pET21-GP, pET21-PGM, pET21-PGI, pET21-P6PE, pET21-P6PP, pET21-AI and pET21-GT. These seven plasmids were converted into *E. coli* BL21 (DE3) (Invitrogen, Carlsbad, CA), and protein expression and purification were carried out, to obtain a multienzyme complex containing the above-mentioned enzymes.

The reaction system was established as follows: 30 mM phosphoric acid buffer (pH 7.0), 5 mM magnesium chloride, 50 g/L maltodextrin, 10 U/mL glutan phosphorylase, 10 U/mL phosphoglucomutase, 10 U/mL glucose phosphate isomerase, 10 U/mL allulose 6-phosphate 3-epimerase, and 10 U/mL allulose 6-phosphate phosphatase, 10 U/mL isoamylase, and 10 U/mL glucan transferase were used to carry out the catalytic reaction at 37° C. for 24 hours, and the final reaction sample was detected by liquid chromatography.

After the reaction, 25 g/L of allulose, and 10 g/L of residual glucose and fructose were obtained.

Example 14 Conversion of Sucrose to Allulose by Extracellular Multienzyme Catalysis To establish an extracellular multienzyme system for converting sucrose into allulose. The key enzymes include: (1) sucrose phosphorylase (EC: 2.4.1.7), which catalyzes the conversion of sucrose to glucose 1-phosphate and fructose, (2) phosphoglucomutase (EC: 5.4.2.2), which catalyzes the conversion of glucose 1-phosphate to glucose 6-phosphate; (3) glucose phosphate isomerase (EC: 5.3.1.9), which catalyzes the conversion of glucose 6-phosphate to fructose 6-phosphate; (4) allulose 6-phosphate 3-epimerase (EC: 5.1.3.-), which catalyzes the conversion of fructose 6-phosphate to allulose 6-phosphate; (5) allulose 6-phosphate phosphatase, which catalyzes the dephosphorylation of allulose 6-phosphate to allulose; (6) glucose isomerase (EC: 5.1.3.5), which catalyzes fructose to be glucose; (7) glucokinase (EC: 2.7.1.2), which catalyzes glucose to glucose 6-phosphate.

In the present disclosure, sucrose phosphorylase was derived from *Bifidobacterium longum* and the gene number on KEGG is BL0536; phosphoglucomutase was derived from *Thermotoga maritima* and the gene number on KEGG is TM0769; glucose phosphate isomerase was derived from *Clostridium thermocellum* and the gene number on KEGG is Cthe0217; allulose 6-phosphate 3-epimerase was derived from *Escherichia coli* and the gene number on KEGG is b4085; allulose 6-phosphate phosphatase was derived from *Escherichia coli* and the gene number on KEGG is b1727; glucose isomerase was derived from *Bacillus licheniformis* and the gene number on KEGG is BL03867; glucokinase was derived from *Microlunatus phosphovorus* and the gene number on KEGG is MLP_2661. These genomic DNAs are available from ATCC official website (www.atcc.org). The seven genes were obtained from the corresponding genomic DNA by PCR using different primers and cloned into the pET21 vector by enzyme digestion and ligation, to obtain corresponding expression vectors: pET21-SP, pET21-PGM, pET21-PGI, pET21-P6PE, pET21-P6PP, pET21-GI, pET21-GK. These seven plasmids were converted into *E. coli* BL21 (DE3) (Invitrogen, Carlsbad, CA), and protein expression and purification were carried out.

The reaction system was established as follows: 30 mM phosphoric acid buffer (pH 7.0), 5 mM magnesium chloride, 5 mM ATP, 30 mM polyphosphate, 20 g/L sucrose, 10 U/mL sucrose phosphorylase, 10 U/mL phosphoglucomutase, 10 U/mL glucose phosphate isomerase, 10 U/mL allulose 6-phosphate 3-epimerase, and 10 U/mL allulose 6-phosphate phosphatase, 10 U/mL glucose isomerase, and 10 U/mL glucokinase were used to carry out the catalytic reaction at 37° C. for 24 hours, and the final reaction sample was detected by liquid chromatography.

After the reaction, 13.4 g/L of allulose, 4.5 g/L of residual sucrose, as well as by-products of 1.4 g/L glucose and 0.7 g/L fructose were obtained.

Example 15 Conversion of Maltodextrin to Allose by Extracellular Multienzyme Catalysis To establish an extracellular multienzyme system for converting maltodextrin into allose. The key enzymes include: (1) glucan phosphorylase (EC: 2.4.1.1), which catalyzes the conversion of glucan to glucose 1-phosphate, (2) phosphoglucomutase (EC: 5.4.2.2), which catalyzes the conversion of glucose 1-phosphate to glucose 6-phosphate; (3) glucose phosphate isomerase (EC: 5.3.1.9), which catalyzes the conversion of glucose 6-phosphate to fructose 6-phosphate; (4) allulose 6-phosphate 3-epimerase (EC: 5.1.3.-), which catalyzes the conversion of fructose 6-phosphate to allulose 6-phosphate; (5) ribose-5-phosphate isomerase (EC: 5.3.1.6), which catalyzes the conversion of allulose 6-phosphate to allose 6-phosphate; (6) allose 6-phosphate phosphatase, which catalyzes the dephosphorylation of allose 6-phosphate to allose; (7) isoamylase (AI), which catalyzes maltodextrin to be a linear glycan; (8) glucan transferase (GT), which catalyzes the polymerization of maltose to produce maltotetraose or oligosaccharides with higher degree of polymerization.

Glucan phosphorylase, phosphoglucomutase, glucose phosphate isomerase, allulose 6-phosphate 3-epimerase, allulose 6-phosphate phosphatase, isoamylase, glucan transferase used were the same as those in Example 13. Ribose-5-phosphate isomerase was derived from *Escherichia coli*, and the gene number on KEGG is b4090 (SEQ ID NO:11). The primers were designed by using genomic DNA derived from *Escherichia coli*, and the corresponding genes were obtained by PCR and cloned into the pET21 vector by enzyme digestion and ligation, to obtain the corresponding expression vector pET21-RPIB. The plasmids were converted into *E. coli* BL21 (DE3) (Invitrogen, Carlsbad, CA), and protein expression and purification were carried out. 30)

The reaction system was established as follows: 30 mM phosphoric acid buffer (pH 7.0), 5 mM magnesium chloride, 50 g/L maltodextrin, 10 U/mL glutan phosphorylase, 10 U/mL phosphoglucomutase, 10 U/mL glucose phosphate isomerase, 10 U/mL allulose 6-phosphate 3-epimerase, 10 U/mL ribose-5-phosphate isomerase, 10 U/mL allose 6-phosphate phosphatase, 10 U/mL isoamylase, and 10 U/mL glucan transferase were used to carry out the catalytic reaction at 37° C. for 24 hours, and the final sample was detected by liquid chromatography.

After the reaction, 15 g/L of allose, 10 g/L allulose, and 10 g/L of residual glucose and fructose were finally obtained.

Example 16 Conversion of Sucrose to Allose by Extracellular Multienzyme Catalysis To establish an extracellular multienzyme system for converting sucrose into allulose. The key enzymes include: (1) sucrose phosphorylase (EC: 2.4.1.7), which catalyzes the conversion of sucrose to glucose 1-phosphate and fructose, (2) phosphoglucomutase (EC: 5.4.2.2), which catalyzes the conversion of glucose 1-phosphate to glucose 6-phosphate; (3) glucose phosphate isomerase (EC: 5.3.1.9), which catalyzes the conversion of glucose 6-phosphate to fructose 6-phosphate; (4) allulose 6-phosphate 3-epimerase (EC: 5.1.3.-), which catalyzes the conversion of fructose 6-phosphate to allulose 6-phosphate; (5) ribose-5-phosphate isomerase (EC: 5.3.1.6), which catalyzes the conversion of allulose 6-phosphate to allose 6-phosphate; (6) allose 6-phosphate phosphatase, which catalyzes the dephosphorylation of allose 6-phosphate to allose; (7) glucose isomerase (EC: 5.1.3.5), which catalyzes fructose to be glucose; (8) glucokinase (EC: 2.7.1.2), which catalyzes glucose to glucose 6-phosphate.

The used sucrose phosphorylase, phosphoglucomutase, glucose phosphate isomerase, allulose 6-phosphate 3-epimerase, allose 6-phosphate phosphatase were the same as those in Example 13. The used glucokinase and glucose 6-phosphate isomerase were the same as those in Example 14. The used ribose-5-phosphate isomerase was the same as that in Example 15. The expressive plasmids containing the above-mentioned genes were converted into *E. coli* BL21 (DE3) (Invitrogen, Carlsbad, CA), and protein expression and purification were carried out.

The reaction system was established as follows: 30 mM phosphoric acid buffer (pH 7.0), 5 mM magnesium chloride, 5 mM ATP, 30 mM polyphosphate, 20 g/L sucrose, 10 U/mL sucrose phosphorylase, 10 U/mL phosphoglucomutase, 10 U/mL glucose phosphate isomerase, 10 U/mL allulose 6-phosphate 3-epimerase, and 10 U/mL ribose-5-phosphate isomerase, 10 U/mL allose 6-phosphate phosphatase, 10 U/mL glucose isomerase and 10 U/mL glucokinase were used to carry out the catalytic reaction at 37° C. for 24 hours, and the final reaction sample was detected by liquid chromatography.

After the reaction, 8.4 g/L of allose, 4.5 g/L of allulose, 3.5 g/L of residual sucrose, as well as by-products of 2.4 g/L glucose and 1.2 g/L fructose were finally obtained.

Example 17 Conversion of Maltodextrin to Allulose by Coupling Extracellular Multienzyme Catalysis and Fermentation 1. Conversion of Maltodextrin to Allulose by Extracellular Multienzyme Catalysis The method for conversion of maltodextrin to allulose by extracellular multienzyme catalysis was the same as that in Example 13.

2. Synthesis of Allulose from Recombinant Strain Allulose5 by Fermentation

A culture medium was prepared by using the reaction solution obtained by extracellular multienzyme catalysis as a carbon source and adding with 10 g/L yeast powder and 10 g/L sodium chloride, and sterilized. According to 2% inoculation amount of the strain, the seed solution of recombinant strain Allulose 5 after overnight cultivation was inoculated into the culture medium. The recombinant *Corynebacterium glutamicum* strain Allulose5 was cultured at 30° C. and 200 rmp for 24 h. After fermentation, the sample was centrifuged at 14000 rmp for 20 min and filtered with a 0.22 μm microporous membrane. The filtrate was analyzed by HPLC.

After fermentation, the yield of allulose increased from 25 g/L to 30 g/L, and allulose was the only sugar in the fermentation liquid, which facilitated the separation of final products.

Example 18 Conversion of Maltodextrin to Allose by Coupling Extracellular Multienzyme Catalysis and Fermentation 1. Conversion of Maltodextrin to Allose by Extracellular Multienzyme Catalysis The method for conversion of maltodextrin to allose by extracellular multienzyme catalysis was the same as that in Example 13.

2. Synthesis of Allose from Recombinant Strain Allose3 by Fermentation

A culture medium was prepared by using the reaction solution obtained by extracellular multienzyme catalysis as a carbon source and adding with 10 g/L yeast powder and 10 g/L sodium chloride, and sterilized. According to 2% inoculation amount of the strain, the seed solution of recombinant strain Allose3 after overnight cultivation was inoculated into the culture medium. The recombinant *Corynebacterium glutamicum* strain Allose3 was cultured at 30° C. and 200 rmp for 24 h. After fermentation, the sample was centrifuged at 14000 rmp for 20 min and filtered with a 0.22 μm microporous membrane. The filtrate was analyzed by HPLC.

After fermentation, the yield of allose increased from 15 g/L to 18 g/L, and the content of allulose increased from 10 g/L to 12 g/L.

The above descriptions are exemplary embodiments of the present disclosure. However, the embodiments are not intended to limit the scope of the present disclosure. Any modification, equivalent alternative, improvement made without departing from the spirit and scope of the present disclosure should fall within the scope of the present disclosure.

The invention claimed is:

1. A method for construction of engineered strains for producing allose, comprising:
enhancing enzyme activities of allulose 6-phosphate 3-epimerase, ribose-5-phosphate isomerase, and allulose 6-phosphate phosphatase in a host cell by introducing genes of allulose 6-phosphate 3-epimerase, ribose-5-phosphate isomerase, and allulose 6-phosphate phosphatase into the host cell; and
reducing enzyme activity of fructose 6-phosphate kinase in the host cell by using molecular genetic manipulation,
wherein said molecular genetic manipulation is gene knockout or introducing a weak promoter into the host cell.

2. The method of claim 1, wherein said engineered strains are obtained by genetic modification of the host cell of bacteria selected from *Corynebacterium glutamate, Escherichia coli, Bacillus subtilis*, lactic acid bacteria, and *Saccharomyces cerevisiae*.

3. The method of claim 1, further comprising enhancing enzyme activities of glucokinase and glucose 6-phosphate isomerase in the host cell by increasing expression strength of the glucokinase and glucose-6-phosphate isomerase genes by introducing into the host cell a strong promoter or using an expression plasmid, or integrating the glucokinase and glucose-6-phosphate isomerase genes with higher enzyme activities from other species by using chromosomal integration.

4. The method of claim 1, further comprising enhancing enzyme activities of fructose permease and fructokinase in the host cell by increasing expression level of fructose permease and fructokinase genes in the host cell by using a strong promoter, chromosomal integration, or an expression plasmid.

5. The method of claim 1, further comprising enhancing enzyme activities of glycerol permease, glycerol dehydrogenase and dihydroxyacetone kinase in the host cell by increasing expression level of glycerol permease, glycerol dehydrogenase, and dihydroxyacetone kinase genes in the host cell by using a strong promoter, chromosomal integration, or an expression plasmid.

* * * * *

SEQUENCE LISTING

<160> NUMBER OF SEQ ID NOS: 50

<210> SEQ ID NO 1
<211> LENGTH: 696
<212> TYPE: DNA
<213> ORGANISM: Escherichia coli

<400> SEQUENCE: 1

```
atgaaaatct cccctcgtt aatgtgtatg gatctgctga aatttaaaga acagatcgaa      60
tttatcgaca gccatgccga ttacttccac atcgatatca tggacggtca ctttgtcccc    120
aatctgacac tctcaccgtt cttcgtaagt caggttaaaa aactggcaac taaaccgctc    180
gactgtcatc tgatggtgac gcggccgcag gattacattg ctcaactggc gcgtgcggga    240
```

```
gcagatttca tcactctgca tccggaaacc atcaacggcc aggcgttccg cctgattgat    300
gaaatccgcc gtcatgacat gaaagtgggg ctgatcctta acccggagac gccagttgag    360
gccatgaaat actatatcca taaggccgat aaaattacgg tcatgactgt cgatcccggc    420
tttgccggac aaccgttcat tcctgaaatg ctggataaac ttgccgaact gaaggcatgg    480
cgtgaacgag aaggtctgga gtacgaaatt gaggtggacg gttcctgcaa ccaggcaact    540
tacgaaaaac tgatggcggc aggggcggat gtctttatcg tcggcacttc cggcctgttt    600
aatcatgcgg aaaatatcga cgaagcatgg agaattatga ccgcgcagat tctggctgca    660
aaaagcgagg tacagcctca tgcaaaaaca gcataa                             696

<210> SEQ ID NO 2
<211> LENGTH: 669
<212> TYPE: DNA
<213> ORGANISM: Escherichia coli

<400> SEQUENCE: 2
atgtcaaccc cgcgtcagat tcttgctgca attttgata tggatggatt acttatcgac     60
tcagaacctt tatgggatcg agccgaactg gatgtgatgg caagcctggg ggtggatatc    120
tcccgtcgta acgagctgcc ggacaccttc ggtttacgca tcgatatggt ggtcgatctt    180
tggtacgccc ggcaaccgtg gaatgggcca agccgtcagg aagtagtaga acgggttatt    240
gcccgtgcca tttcactggt tgaagagaca cgtccattat taccaggcgt gcgcgaagcc    300
gttgcgttat gcaaagaaca aggtttattg gtgggactgg cctccgcgtc accactacat    360
atgctggaaa aagtgttgac catgtttgac ttacgcgaca gttcgatgc cctcgcctcg    420 gccgaaaaac tgccttacag caagccgcat ccgcaagtat atctcgactg cgcagcaaaa    480
ctgggcgttg accctctgac ctgcgtagcg ctggaagatt cggtaaatgg catgatcgcc    540
tctaaagcag cccgcatgcg ttccatcgtc gttcctgcgc agaagcgca aaatgatcca    600 cgttttgtat tagcagacgt caaactttca tcgctgacag aactcaccgc aaaagacctt    660
ctcggttaa                                                           669

<210> SEQ ID NO 3
<211> LENGTH: 1041
<212> TYPE: DNA
<213> ORGANISM: Corynebacterium glutamicum

<400> SEQUENCE: 3
atggaagaca tgcgaattgc tactctcacg tcaggcggcg actgcccegg actaaacgcc     60 gtcatccgag gaatcgtccg cacagccagc aatgaatttg ctccaccgt cgttggttat    120 caagacggtt gggaaggact gttaggcgat cgtcgcgtac agctgtatga cgatgaagat    180
attgaccgaa tcctccttcg aggcggcacc attttgggca ctggtcgcct ccatccggac    240
aagtttaagg ccggaattga tcagattaag gccaacttag aagacgccgg catcgatgcc    300
cttatcccaa tcggtggcga aggaaccctg aagggtgcca gtggctgtc tgataacggt    360 atccctgttg tcggtgtccc aaagaccatt gacaatgacg tgaatggcac tgacttcacc    420 tttcggtttcg atactgctgt ggcagtggct accgacgctg ttgaccgcct gcacaccacc    480
gctgaatctc acaaccgtgt gatgatcgtg gaggtcatgg gccgccacgt gggttggatt    540
gctctgcacg caggtatggc cggcggtgct cactacaccg ttattccaga agtacctttc    600
gatattgcag agatctgcaa ggcgatggaa cgtcgcttcc agatgggcga agtacggc     660 attatcgtcg ttgcggaagg tgcgttgcca cgcgaaggca ccatggagct tcgtgaaggc    720
```

```
cacattgacc agttcggtca caagaccttc acgggaattg acagcagat cgctgatgag    780 atccacgtgc gcctcggcca cgatgttcgt acgaccgttc ttggccacat tcaacgtggt    840
ggaaccccaa ctgctttcga ccgtgttctg gccactcgtt atggtgttcg tgcagctcgt    900
gcgtgccatg agggaagctt tgacaaggtt gttgctttga agggtgagag cattgagatg    960
atcacctttg aagaagcagt cggaaccttg aaggaagttc cattcgaacg ctgggttact   1020
gcccaggcaa tgtttggata g                                              1041
```

<210> SEQ ID NO 4
<211> LENGTH: 972
<212> TYPE: DNA
<213> ORGANISM: Corynebacterium glutamicum

<400> SEQUENCE: 4

```
atgccacaaa aaccggccag tttcgcggtg ggctttgaca tcggcggcac caacatgcga     60
gccgggcttg tcgacgaatc cgggcgcatc gtgaccagtt tgtcggcgcc gtcgccgcgc    120
acgacgcagg caatggaaca ggggattttt gatctagtcg aacagctcaa ggccgaatac    180
ccggttggtg ctgtgggact tgccgtcgcg ggatttttgg atcctgagtg cgaggttgtt    240
cgatttgccc cgcaccttcc ttggcgcgat gagccagtgc gtgaaaagtt ggaaaacctt    300
ttgggcctgc ctgttcgttt ggaacatgat gccaactcag cagcgtgggg tgagcatcgt    360
tttggtgcag ctcaaggcgc tgacaactgg gttttgttgg cactcggcac tggaattggt    420
gcagcgctga ttgaaaaagg cgaaatttac cgtggtgcat atggcacggc accagaattt    480
ggtcatttgc gtgttgttcg tggcggacgc gcatgtgcgt gtggcaaaga aggctgcctg    540
gagcgttact gttccggtac tgccttggtt tacactgcgc gtgaattggc ttcgcatggc    600
tcattccgca acagcgggct gtttgacaag atcaaagccg atccgaattc catcaatgga    660
aaaacgatca ctgcggcagc gcgccaagaa gacccacttg ctctcgccgt tctggaagat    720
ttcagcgagt ggctgggcga aactttggcg atcattgctg atgtccttga cccaggcatg    780
atcatcattg gtggcggact gtccaatgct gccgaccttt atttggatcg ctcggtcaac    840
cactattcca cccgcatcgt cggcgcagga tatcgccctt ggcacgcgt tgccacagct    900 cagttgggtg cggatgctgg catgatcggt gtcgctgatc tagctcgacg ctctgtagtg    960
gaagccaact ag                                                        972
```

<210> SEQ ID NO 5
<211> LENGTH: 1623
<212> TYPE: DNA
<213> ORGANISM: Corynebacterium glutamicum

<400> SEQUENCE: 5

```
atggcggaca tttcgaccac ccaggtttgg caagacctga ccgatcatta ctcaaacttc     60
caggcaacca ctctgcgtga acttttcaag gaagaaaacc gcgccgagaa gtacaccttc    120
tccgcggctg gcctccacgt cgacctgtcg aagaatctgc ttgacgacgc caccctcacc    180
aagctccttg cactgaccga gaatctggcc ttcgcgaac gcattgacgc gatgtttgcc    240
ggtgaacacc tcaacaacac cgaagaccgc gctgtcctcc acaccgcgct gcgccttcct    300
gccgaagctg atctgtcagt agatggccaa gatgttgctg ctgatgtcca cgaagttttg    360
ggacgcatgc gtgacttcgc tactgcgctg cgctcaggca actggttggg acacaccggc    420
cacacgatca agaagatcgt caacattggt atcggtggct ctgacctcgg accagccatg    480
```

-continued

```
gctacgaagg ctctgcgtgc atacgcgacc gctggtatct cagcagaatt cgtctccaac      540
gtcgacccag cagacctcgt ttctgtgttg aagacctcg atgcagaatc acattgttc       600 gtgatcgctt cgaaaacttt caccacccag agacgctgt ccaacgctcg tgcagctcgt      660
gcttggctgg tagagaagct cggtgaagag gctgtcgcga agcacttcgt cgcagtgtcc      720
accaatgctg aaaaggtcgc agagttcggt atcgacacgg acaacatgtt cggcttctgg      780
gactgggtcg gaggtcgtta ctccgtggac tccgcagttg gtcttttccct catggcagtg     840 atcggccctc gcgacttcat gcgtttcctc ggtggattcc acgcgatgga tgaacacttc      900
cgcaccacca agttcgaaga gaacgttcca atcttgatgg ctctgctcgg tgtctggtac      960
tccgatttct atggtgcaga acccacgct gtcctaccct attccgagga tctcagccgt     1020
tttgctgctt acctccagca gctgaccatg gaatcaaatg gcaagtcagt ccaccgcgac    1080
ggctcccctg tttccactgg cactggcgaa atttactggg gtgagcctgg cacaaatggc    1140
cagcacgctt tcttccagct gatccaccag ggcactcgcc ttgttccagc tgatttcatt    1200
ggtttcgctc gtccaaagca ggatcttcct gccggtgagc gcaccatgca tgaccttttg    1260
atgagcaact tcttcgcaca gaccaaggtt ttggctttcg gtaagaacgc tgaagagatc    1320
gctgcgaagg tgtcgcacc tgagctggtc aaccacaagg tcatgccagg taatcgccca    1380
accaccacca ttttggcgga ggaacttacc ccttctattc tcggtgcgtt gatcgctttg    1440
tacgaacaca tcgtgatggt tcagggcgtg atttgggaca tcaactcctt cgaccaatgg    1500
ggtgttgaac tgggcaaaca gcaggcaaat gacctcgctc cggctgtctc tggtgaagag    1560
gatgttgact cgggagattc ttccactgat tcactgatta agtggtaccg cgcaaatagg    1620
tag                                                                  1623
```

<210> SEQ ID NO 6
<211> LENGTH: 1427
<212> TYPE: DNA
<213> ORGANISM: Zymomonas mobilis

<400> SEQUENCE: 6

```
atggcggaca tttcgaccac ccaggtttgg caagacctga ccgatcatta ctcgctgcta      60
taggcggctt gcttttcggt tacgattcag cggttatcgc tgcaatcggt acaccggttg    120
atatccattt tattgccccct cgtcacctgt ctgctacggc tgcggcttcc ctttctggga    180
tggtcgttgt tgctgttttg gtcggttgtg ttaccggttc tttgctgtct ggctggattg    240
gtattcgctt cggtcgtcgc ggcggattgt tgatgagttc catttgtttc gtcgccgccg    300
gttttggtgc tgcgttaacc gaaaaattat ttggaaccgg tggttcggct ttacaaattt    360
tttgcttttt ccggtttctt gccggtttag gtatcggtgt cgtttcaacc ttgacccccaa    420 cctatattgc tgaaattcgt ccgccagaca acgtggtca gatggtttct ggtcagcaga    480
tggccattgt gacgggtgct ttaaccggtt atatctttac ctggttactg gctcatttcg    540
gttctatcga ttgggttaat gccagtggtt ggtgctggtc tccggcttca gaaggcctga    600
tcggtattgc cttcttattg ctgctgttaa ccgcaccgga tacgccgcat ggttggtga    660 tgaagggacg tcattccgag gctagcaaaa tccttgctcg tctggaaccg caagccgatc    720
ctaatctgac gattcaaaag attaaagctg ctttgataa agccatggac aaaagcagcg    780
caggtttgtt tgcttttggt atcaccgttg ttttgccgg tgtatccgtt gctgccttcc    840
agcagttagt cggtattaac gccgtgctgt attatgcacc gcagatgttc cagaatttag    900
gttttggagc tgatacggca ttattgcaga ccatctctat cggtgttgtg aacttcatct    960
```

```
tcaccatgat tgcttcccgt gttgttgacc gcttcggccg taaacctctg cttatttggg      1020
gtgctctcgg tatggctgca atgatggctg ttttaggctg ctgtttctgg ttcaaagtcg      1080
gtggtgtttt gcctttggct tctgtgcttc tttatattgc agtctttggt atgtcatggg      1140
gccctgtctg ctgggttgtt ctgtcagaaa tgttcccgag ttccatcaag ggcgcagcta      1200
tgcctatcgc tgttaccgga caatggttag ctaatatctt ggttaacttc ctgtttaagg      1260
ttgccgatgg ttctccagca ttgaatcaga ctttcaacca cggtttctcc tatctcgttt      1320
tcgcagcatt aagtatctta ggtggcttga ttgttgctcg cttcgtgccg gaaaccaaag      1380
gtcggagcct ggatgaaatc gaggagatgt ggcgctccca gaagtag                    1427

<210> SEQ ID NO 7
<211> LENGTH: 879
<212> TYPE: DNA
<213> ORGANISM: Enterococcus faecalis(Enterococcus faecalis)

<400> SEQUENCE: 7
atgacagaaa aacttttagg aagtatcgaa gccggtggca caaaatttgt atgtggcgtt       60
gggacagatg atttgaccat cgtagaacgt gtcagttttc ccacaacaac cccagaagaa      120
acaatgaaaa agtaataga attttttccaa caatatcctt taaaagcgat tgggattggt      180
tcatttggtc cgattgatat tcacgttgat tctcctacgt atggttatat cacttctaca      240
ccaaaattag cttggcgtaa cttttgacttg ttaggaacta tgaaacaaca ttttgatgtg      300
ccaatggctt ggacaacgga tgtgaatgct gcggcatatg gtgagtatgt tgctggaaat      360
gggcaacata catcctagttg tgtatattat acaattggaa ctggtgttgg cgctggagcg      420
attcaaaacg gtgagtttat tgaaggcttt agccacccag aaatggggca tgcgttagtt      480
cgtcgtcatc ctgaagatac gtatgcagga aattgtcctt atcatggaga ttgtttagaa      540
gggattgcag caggaccagc agttgaaggt cgttctggta aaaaaggaca tttattggaa      600
gaggatcata aaacttggga attagaagct tattatttag cgcaagcggc gtacaatacg      660
actttattat tagcgccaga agtgatcatt ttaggtggcg gcgtcatgaa acaacgtcat      720
ttgatgccga aagttcgtga aaaatttgct gaattagtca atggatatgt ggaaacaccg      780
cctttagaaa aatacttggt gacgcctctt ttagaagata tccaggaac aatcggttgc       840 tttgccttgg caaaaaaagc tttaatggct caaaaataa                             879

<210> SEQ ID NO 8
<211> LENGTH: 846
<212> TYPE: DNA
<213> ORGANISM: Escherichia coli

<400> SEQUENCE: 8
atgagtcaaa catcaaccct gaaaggccag tgcattgctg aattcctcgg taccgggttg       60
ttgattttct tcggtgtggg ttgcgttgca gcactaaaag tcgctggtgc gtcttttggt      120
cagtgggaaa tcagtgtcat ttggggactg ggggtggcaa tggccatcta cctgaccgca      180
ggggtttccg cgcgcatct taatcccgct gttaccattg cattgtggct gtttgcctgt      240
ttcgacaagc gcaaagttat tccttttatc gtttcacaag ttgccggcgc tttctgtgct      300
gcggctttag tttacgggct ttactacaat ttattttttcg acttcgagca gactcatcac      360
attgttcgcg gcagcgttga aagtgttgat ctggctggca cttctctctac ttaccctaat      420 cctcatatca attttgtgca ggctttcgca gttgagatgg tgattaccgc tattctgatg      480
```

```
gggctgatcc tggcgttaac ggacgatggc aacggtgtac cacgcggccc tttggctccc    540
ttgctgattg gtctactgat tgcggtcatt ggcgcatcta tgggcccatt gacaggtttt    600
gccatgaacc cagcgcgtga cttcggtccg aaagtctttg cctggctggc gggctggggc    660
aatgtcgcct ttaccggcgg cagagacatt ccttacttcc tggtgccgct tttcggccct    720
atcgttggcg cgattgtagg tgcatttgcc taccgcaaac tgattggtcg ccatttgcct    780
tgcgatatct gtgttgtgga agaaaaggaa accacaactc cttcagaaca aaaagcttcg    840
ctgtaa                                                               846

<210> SEQ ID NO 9
<211> LENGTH: 1098
<212> TYPE: DNA
<213> ORGANISM: Klebsiella pneumoniae

<400> SEQUENCE: 9
atgctaaaag ttattcaatc tccagccaaa tatctccagg gaccggatgc atccacgttg     60
tttggcgaat acgctaaaaa cctggcggac agcttttttcg tgattgccga tgacttcgtg    120
atgaagctgg cgggtgagaa agtgttgaac ggtttgcata gccacaatat cagctgccat    180
gcggagcgct tcaacggcga gtgcagccac gttgagatca atcgcctgat cgccattctg    240
aagcagcacg gctgccgcgg cgtggtgggc atcggcggcg gcaagacgct cgatacggcg    300
aaagcgatag gctattacca gaagctgccg gtggtggtga tcccgacgat tgcctccacc    360
gatgcgccaa ccagcgcgtt gtcggttatt tataccgaag ccggtgaatt tgaagagtat    420
cttatttacc cgaaaaatcc ggacatggtg gtgatggata cggcgattat cgctaaagcc    480
ccggtacgcc tgctggtggc cgggatgggc gatgcgcttt caacctggtt tgaagccagg    540
gcctgctatg acgccagagc caccagcatg gccggcggcc agtcgacggc ggcggcgctg    600
agcctggcgc gcctgtgcta tgatacgctg ctggcggaag gcgaaaaggc ccgccttgcc    660
gctcaggccg gagtggtgac cgatgcgctc gaacgcatcg ttgaagcgaa tacctacctt    720
agcggaattg gctttgaaag cagcggcctg gccgccgcgc acgccattca caatggtttc    780
accatcctcg aagagtgtca ccacctgtac catggcgaga agtcgcgtt tggtaccctg    840 gcgcagctgg tgctgcaaaa tagcccgatg gaagagatcg aaacggtgct gaacttctgc    900
cataccgtcg gcctgccggt cacgctggcg caaatgggcg ttaaagaggg catcgacgag    960
aaaattcagg cggtagcaaa agcgacctgt gcggaaggcg aaaccatcca taacatgccg    1020
ttcccggtca gcgcgcagag cgtgcatgcg gcaattctga ccgccgacct gcttggacag    1080
cagtggctgg cgcgttaa                                                 1098

<210> SEQ ID NO 10
<211> LENGTH: 1659
<212> TYPE: DNA
<213> ORGANISM: Citrobacter freundii

<400> SEQUENCE: 10
atgtctcaat tcttttttaa ccaacgcacc catctcgtga gcgacgtcat cgacggggcg     60
attatcgcca gccatggaa taacctgggg cgtctggaaa gcgatccggc cattcgcatc    120
gtggtccgtc gtgaccttaa taaaataac gtagcggtca tttccggcgg cggttcggga    180
cacgaacccg cacacgttgg gttttatcggt aaaggcatgc taaccgctgc ggtctgcggc    240
gacgttttcg cctccccgag cgtggatgca gtactgaccg cgattcaggc ggtgaccggt    300
gaggctggct gtttgttgat tgtgaaaaac tacaccggtg accgtcttaa tttcggtctc    360
```

```
gccgccgaga aggcgcgtcg ccttggctat aacgttgaaa tgctgattgt cggcgacgac    420
atctccctgc cggataacaa acacccacgt ggcattgcgg gaactatcct ggtgcataaa    480
atcgcaggct attttgccga acgcggctat aacctcgcca ccgtcctgcg tgaagcgcag    540
tacgcagcca gcaacacctt tagcctgggc gtagctcttt ccagctgtca tctgccgcaa    600
gaaaccgacg ccgcccctcg tcatcatccg ggtcatgcgg agctgggtat gggcattcac    660
ggcgaaccag gcgcatcggt tatcgacacc caaaacagtg cgcaagtggt gaacctgatg    720
gtggataaac tgctggccgc cctgcctgaa accggtcgtc tggcggtgat gattaataac    780
cttggcggcg tttccgtggc cgaaatggcc atcatcaccc gcgaactcgc cagcagcccg    840
ctgcactcgc gtatcgactg gctaattggc ccggcctcgc tggtcaccgc actggatatg    900
aaaggcttct cactgacggc catcgtgctg aagagagca tcgaaaaagc actgctcacc    960
gaagtggaaa ccagcaactg gccgacgccg gtcccaccgc gtgaaatcac ctgcgtagtg   1020
tcatctcagc gtagcgcccg cgtggaattc cagccttcgg caaacgccct ggtggccggg   1080
attgtggagc tggtcaccgc aacccttcc gatctggaga ctcatctgaa tgcgctggac   1140
gccaaagtcg gcgatggcga taccggttcg acctttgccg ccggcgcgcg tgaaattgcc   1200
agcctgctgc atcgccagca gctgccgctg gataaccttg ccacgctgtt cgcgctgatt   1260
ggcgaacgtc tgaccgtggt gatgggcggt ccagcggtg tgctgatgtc aatcttcttt    1320
accgccgccg ggcagaaact ggaacagggc gctaacgttg tcgaagcgct aaatacgggg   1380
ctggcgcaga tgaagttcta cggcggcgca gacgaaggcg atcgcacgat gattgatgcg   1440
ctgcaaccgg ccctgacctc tctgcttaca cagccgaaaa atctgcaggc cgcattcgac   1500
gccgcgcaag cgggagccga acgaacctgt tgtcgagca aagccaatgc gggtcgcgca   1560
tcgtatctga gcagcgaaag cctactcgga aatatggacc ccggcgcgca cgccgtagcg   1620
atggtgttta agcgctggc ggagagtgag ctgggctaa                           1659

<210> SEQ ID NO 11
<211> LENGTH: 450
<212> TYPE: DNA
<213> ORGANISM: Escherichia coli

<400> SEQUENCE: 11
atgaaaaaga ttgcatttgg ctgtgatcat gtcggtttca ttttaaaaca tgaaatagtg     60
gcacatttag ttgagcgtgg cgttgaagtg attgataaag gaacctggtc gtcagagcgt    120
actgattatc acattacgc cagtcaagtc gcactggctg ttgctggcgg agaggttgat    180
ggcgggattt tgatttgtgg tactggcgtc ggtatttcga tagcggcgaa caagtttgcc    240
ggaattcgcg cggtcgtctg tagcgaacct tattccgcgc aactttcgcg gcagcataac    300
gacaccaacg tgctggcttt tggttcacga gtggttggcc tcgaactggc aaaaatgatt    360
gtggatgcgt ggctgggcgc acagtacgaa ggcgtcgtc atcaacaacg cgtggaggcg    420
attacggcaa tagagcagcg gagaaattga                                     450

<210> SEQ ID NO 12
<211> LENGTH: 750
<212> TYPE: DNA
<213> ORGANISM: Klebsiella oxytoca( Klebsiella oxytoca)

<400> SEQUENCE: 12
atgaaccact ctgtctcctc tatgaatact tcccttagcg gtaaagtcgc cgccattacc     60
```

```
ggcgcggcgt ccggtatcgg cctcgaatgc gccagaaccc tgctgggcgc tggcgcaaaa    120
gtggtgctta tcgaccgtga aggcgagaag ctcaacaaac ttgtcgccga actcggcgaa    180
aacgccttcg ccctgcaggt tgacctgatg caggcggatc aggtcgataa tattctgcag    240
ggtattttgc agcttaccgg gcgtctcgat attttccacg ccaacgccgg agcttacatc    300
ggcgggccgg tggcagaggg cgatccggac gtctgggacc gcgtgctgca cctcaacacc    360
aacgccgcct ccgctgcgt gcgcagcgtc ctgccgcatc ttatcgcgca aaagtccggg      420
gacattatct tcaccagctc tatcgcgggg gtggtgccgg tgatctggga gcctatctat    480
accgcgtcga aatttgccgt ccaggcgttt gttcatacta cccgccgcca ggtttcgcag    540
tacggcgtgc gcgtcggcgc cgtgctgccg ggcccggtgg tcaccgccct gctggacgac    600
tggccgaaag ccaaaatgga cgaagcgctg ccaacggca gcctgatgca gccgattgag      660
gtggccgagt cggtgctgtt tatggtgacg cgctcgaaaa acgtcaccgt acgcgacatt    720
gtgatcctgc cgaacagcgt ggatctctga                                     750

<210> SEQ ID NO 13
<211> LENGTH: 809
<212> TYPE: DNA
<213> ORGANISM: Corynebacterium glutamicum

<400> SEQUENCE: 13
aatgattttg gtttccttct gcagttcgc catgtgactg cggtaaaact gccccggaac       60
cggaatatct cgacgccaca gaacgccatt tgcgggcctt aacacccgt gggcatacct      120
tttacccatt ccagatattc ggtcgcttaa attgccagt gtgattccaa acagaaatct       180
ggggcgacct ctaataagag tcgccccgat aagtttttt accgtaatta ttactgggag       240
tcagatactg cgtaagcaat cgcagcagcg ccagcggtca cagtaagaac tgcaggccac    300
gcgccaatct tcttggcaag tgggtgggac aggccaaatg caccaacgta ggttgccagc    360
aggccagtag ctactgcagg acccttcttt tcattccagc ttcgtgcagc aagcgctccg    420
gatgctgcca atggaatggt gcccagtggg cgaatgccgg attcacgggc agtcaaccaa    480
ccgccgatca aacctgctgc gacgacggtg gcagtgctga cctgggatgc cttttttcaat   540
ttcatttcca tggtgagcca gtctagagac aaaattttc cgcgggggtt tcttgatct      600
gatccgacaa cccaatgggg gcaaaaatgt gtccgaccaa aaattgtgca gcacaccaca    660
tgcccgctcg acaatgtcg atttgttaat gaaactgcag ctctggcgat taaataagat     720
ggtcagagac agttttttgg cctgtcaacc cctgtgattc tcttattttt gggtgattgt    780
tccggcgcgg gtgttgtgat gggtttaat                                     809

<210> SEQ ID NO 14
<211> LENGTH: 869
<212> TYPE: DNA
<213> ORGANISM: Corynebacterium glutamicum

<400> SEQUENCE: 14
tttttcgggc ttttatcaac agccaataac agctctttcg cccattgagg tggaggggct     60
gttttttcat gccgtaagga aagtgcaagt aagtgaaatc aagtggccta gatccattga    120
cacttagact gtgacctagg cttgactttc gtggggagt ggggataagt tcatcttaaa     180
cacaatgcaa tcgattgcat ttacgttcct tatcccacaa taggggtacc ttccagaaag   240
ttggtgagga gatggcttcc gaaacctcca gcccgaagaa gcgggccacc acgctcaaag    300
acatcgcgca agcaacacag ctttcagtca gcacggtgtc ccgggcattg gccaacaacg    360
```

```
cgagcattcc ggaatccaca cgcatccgag tggttgaagc cgctcaaaag ctgaactacc    420
gtcccaatgc ccaagctcgt gcattgcgga agtcgaggac agacaccatc ggtgtcatca    480
ttccaaacat tgagaaccca tatttctcct cactagcagc atcgattcaa aaagctgctc    540
gtgaagctgg ggtgtccacc attttgtcca actctgaaga aaacccagag ctgcttggtc    600
agactttggc gatcatggat gaccaacgcc tcgatggaat catcgtggtg ccacacattc    660
agtcagagga acaagtcact gacttggtta acaggggagt gccagtagtg ctggcagacc    720
gtagttttgt taactcgtct attccttcgg ttacctcaga tccagttccg ggcatgactg    780
aagctgtgga cttactcctg gcagctgacg tgcaattggg ctaccttgcc ggcccgcagg    840
atacttccac tggtcagctg cgtcttaac                                      869
```

<210> SEQ ID NO 15
<211> LENGTH: 35
<212> TYPE: DNA
<213> ORGANISM: artificial sequence
<220> FEATURE:
<223> OTHER INFORMATION: synthesized

<400> SEQUENCE: 15
taccggaatt catgaaaatc tccccctcgt taatg    35

<210> SEQ ID NO 16
<211> LENGTH: 34
<212> TYPE: DNA
<213> ORGANISM: artificial sequence
<220> FEATURE:
<223> OTHER INFORMATION: synthesized

<400> SEQUENCE: 16
gatcccccgg gttatgctgt ttttgcatga ggct    34

<210> SEQ ID NO 17
<211> LENGTH: 48
<212> TYPE: DNA
<213> ORGANISM: artificial sequence
<220> FEATURE:
<223> OTHER INFORMATION: synthesized

<400> SEQUENCE: 17
gatggtctag aaaaggagga caaccatgtc aaccccgcgt cagattct    48

<210> SEQ ID NO 18
<211> LENGTH: 35
<212> TYPE: DNA
<213> ORGANISM: artificial sequence
<220> FEATURE:
<223> OTHER INFORMATION: synthesized

<400> SEQUENCE: 18
gacaactgca gttaaccgag aaggtctttt gcggt    35

<210> SEQ ID NO 19
<211> LENGTH: 33
<212> TYPE: DNA
<213> ORGANISM: artificial sequence
<220> FEATURE:
<223> OTHER INFORMATION: synthesized

<400> SEQUENCE: 19
accggaattc atgatttggg tttccttctg cga    33

<210> SEQ ID NO 20
<211> LENGTH: 43
<212> TYPE: DNA
<213> ORGANISM: artificial sequence
<220> FEATURE:
<223> OTHER INFORMATION: synthesized

<400> SEQUENCE: 20
ttcgaatgga acttccttca agctggctgt gcggacgatt cct                    43

<210> SEQ ID NO 21
<211> LENGTH: 45
<212> TYPE: DNA
<213> ORGANISM: artificial sequence
<220> FEATURE:
<223> OTHER INFORMATION: synthesized

<400> SEQUENCE: 21
aggaatcgtc cgcacagcca gcttgaagga agttccattc gaacg                  45

<210> SEQ ID NO 22
<211> LENGTH: 32
<212> TYPE: DNA
<213> ORGANISM: artificial sequence
<220> FEATURE:
<223> OTHER INFORMATION: synthesized

<400> SEQUENCE: 22
actcaagctt gttaagacgc agctgaccag tg                                32

<210> SEQ ID NO 23
<211> LENGTH: 40
<212> TYPE: DNA
<213> ORGANISM: artificial sequence
<220> FEATURE:
<223> OTHER INFORMATION: synthesized

<400> SEQUENCE: 23
cactcaagct tatgggatcc atggcggaca tttcgaccac                        40

<210> SEQ ID NO 24
<211> LENGTH: 34
<212> TYPE: DNA
<213> ORGANISM: artificial sequence
<220> FEATURE:
<223> OTHER INFORMATION: synthesized

<400> SEQUENCE: 24
gacaactgca gctacctatt tgcgcggtac cact                              34

<210> SEQ ID NO 25
<211> LENGTH: 47
<212> TYPE: DNA
<213> ORGANISM: artificial sequence
<220> FEATURE:
<223> OTHER INFORMATION: synthesized

<400> SEQUENCE: 25
gacaactgca gaaaggagga caaccatgcc acaaaaaccg gccagtt                47

<210> SEQ ID NO 26
<211> LENGTH: 34
<212> TYPE: DNA
<213> ORGANISM: artificial sequence
<220> FEATURE:
<223> OTHER INFORMATION: synthesized

```
<400> SEQUENCE: 26
gatggtctag attagttggc ttccactaca gagc                               34

<210> SEQ ID NO 27
<211> LENGTH: 32
<212> TYPE: DNA
<213> ORGANISM: artificial sequence
<220> FEATURE:
<223> OTHER INFORMATION: synthesized

<400> SEQUENCE: 27
gatggtctag atggccgtta ccctgcgaat gt                                 32

<210> SEQ ID NO 28
<211> LENGTH: 46
<212> TYPE: DNA
<213> ORGANISM: artificial sequence
<220> FEATURE:
<223> OTHER INFORMATION: synthesized

<400> SEQUENCE: 28
agtacccaga ttttccatt cattgtatgt cctcctggac ttcgtg                   46

<210> SEQ ID NO 29
<211> LENGTH: 46
<212> TYPE: DNA
<213> ORGANISM: artificial sequence
<220> FEATURE:
<223> OTHER INFORMATION: synthesized

<400> SEQUENCE: 29
cacgaagtcc aggaggacat acaatgaatg gaaaaatctg ggtact                  46

<210> SEQ ID NO 30
<211> LENGTH: 47
<212> TYPE: DNA
<213> ORGANISM: artificial sequence
<220> FEATURE:
<223> OTHER INFORMATION: synthesized

<400> SEQUENCE: 30
accctgacta ctttcagaac tcattcacag cgagcgctga agatcgt                 47

<210> SEQ ID NO 31
<211> LENGTH: 61
<212> TYPE: DNA
<213> ORGANISM: artificial sequence
<220> FEATURE:
<223> OTHER INFORMATION: synthesized

<400> SEQUENCE: 31
acgatcttca gcgctcgctg tgaaaaggag gacaaccatg agttctgaaa gtagtcaggg   60
t                                                                  61

<210> SEQ ID NO 32
<211> LENGTH: 26
<212> TYPE: DNA
<213> ORGANISM: artificial sequence
<220> FEATURE:
<223> OTHER INFORMATION: synthesized

<400> SEQUENCE: 32
ctacttctgg gagcgccaca tctcct                                       26
```

<210> SEQ ID NO 33
<211> LENGTH: 50
<212> TYPE: DNA
<213> ORGANISM: artificial sequence
<220> FEATURE:
<223> OTHER INFORMATION: synthesized

<400> SEQUENCE: 33
gatggtctag aaaaggagga caaccatgag tcaaacatca accttgaaag                50

<210> SEQ ID NO 34
<211> LENGTH: 56
<212> TYPE: DNA
<213> ORGANISM: artificial sequence
<220> FEATURE:
<223> OTHER INFORMATION: synthesized

<400> SEQUENCE: 34
gagattgaat aacttttagc atatctatat ctccttatta cagcgaagct ttttgt         56

<210> SEQ ID NO 35
<211> LENGTH: 56
<212> TYPE: DNA
<213> ORGANISM: artificial sequence
<220> FEATURE:
<223> OTHER INFORMATION: synthesized

<400> SEQUENCE: 35
acaaaaagct tcgctgtaat aaggagatat agatatgcta aaagttattc aatctc         56

<210> SEQ ID NO 36
<211> LENGTH: 60
<212> TYPE: DNA
<213> ORGANISM: artificial sequence
<220> FEATURE:
<223> OTHER INFORMATION: synthesized

<400> SEQUENCE: 36
tggttaaaaa agaattgaga catggttgtc ctcctttta acgcgccagc cactgctgtc      60

<210> SEQ ID NO 37
<211> LENGTH: 60
<212> TYPE: DNA
<213> ORGANISM: artificial sequence
<220> FEATURE:
<223> OTHER INFORMATION: synthesized

<400> SEQUENCE: 37
gacagcagtg gctggcgcgt taaaaggag acaaccatg tctcaattct ttttaacca        60

<210> SEQ ID NO 38
<211> LENGTH: 36
<212> TYPE: DNA
<213> ORGANISM: artificial sequence
<220> FEATURE:
<223> OTHER INFORMATION: synthesized

<400> SEQUENCE: 38
tcccccgggt ctagattagc ccagctcact ctccgc                               36

<210> SEQ ID NO 39
<211> LENGTH: 35
<212> TYPE: DNA
<213> ORGANISM: artificial sequence
<220> FEATURE:
<223> OTHER INFORMATION: synthesized

<400> SEQUENCE: 39
taccggaatt catgaaaatc tccccctcgt taatg					35

<210> SEQ ID NO 40
<211> LENGTH: 56
<212> TYPE: DNA
<213> ORGANISM: artificial sequence
<220> FEATURE:
<223> OTHER INFORMATION: synthesized

<400> SEQUENCE: 40
gaatctgacg cggggttgac atggttgtcc tccttttat gctgtttttg catgag			56

<210> SEQ ID NO 41
<211> LENGTH: 56
<212> TYPE: DNA
<213> ORGANISM: artificial sequence
<220> FEATURE:
<223> OTHER INFORMATION: synthesized

<400> SEQUENCE: 41
ctcatgcaaa aacagcataa aaaggaggac aaccatgtca accccgcgtc agattc			56

<210> SEQ ID NO 42
<211> LENGTH: 61
<212> TYPE: DNA
<213> ORGANISM: artificial sequence
<220> FEATURE:
<223> OTHER INFORMATION: synthesized

<400> SEQUENCE: 42
atcacagcca aatgcaatct ttttcatggt tgtcctcctt tttaaccgag aaggtctttt			60 g											61

<210> SEQ ID NO 43
<211> LENGTH: 61
<212> TYPE: DNA
<213> ORGANISM: artificial sequence
<220> FEATURE:
<223> OTHER INFORMATION: synthesized

<400> SEQUENCE: 43
caaaagacct tctcggttaa aaaggaggac aaccatgaaa agattgcat ttggctgtga			60 t											61

<210> SEQ ID NO 44
<211> LENGTH: 35
<212> TYPE: DNA
<213> ORGANISM: artificial sequence
<220> FEATURE:
<223> OTHER INFORMATION: synthesized

<400> SEQUENCE: 44
gacaactgca gttaaccgag aaggtctttt gcggt					35

<210> SEQ ID NO 45
<211> LENGTH: 35
<212> TYPE: DNA
<213> ORGANISM: artificial sequence
<220> FEATURE:
<223> OTHER INFORMATION: synthesized

<400> SEQUENCE: 45

```
taccggaatt catgaaaatc tccccctcgt taatg                                35
```

<210> SEQ ID NO 46
<211> LENGTH: 56
<212> TYPE: DNA
<213> ORGANISM: artificial sequence
<220> FEATURE:
<223> OTHER INFORMATION: synthesized

<400> SEQUENCE: 46

```
gaatctgacg cggggttgac atggttgtcc tccttttat gctgttttg catgag          56
```

<210> SEQ ID NO 47
<211> LENGTH: 61
<212> TYPE: DNA
<213> ORGANISM: artificial sequence
<220> FEATURE:
<223> OTHER INFORMATION: synthesized

<400> SEQUENCE: 47

```
ctcatgcaaa aacagcataa aaaggaggac aaccatgaaa aagattgcat ttggctgtga    60
t                                                                    61
```

<210> SEQ ID NO 48
<211> LENGTH: 54
<212> TYPE: DNA
<213> ORGANISM: artificial sequence
<220> FEATURE:
<223> OTHER INFORMATION: synthesized

<400> SEQUENCE: 48

```
caaaagacct tctcggttaa ggttgtcctc cttttaacc gagaaggtct tttg           54
```

<210> SEQ ID NO 49
<211> LENGTH: 57
<212> TYPE: DNA
<213> ORGANISM: artificial sequence
<220> FEATURE:
<223> OTHER INFORMATION: synthesized

<400> SEQUENCE: 49

```
ccaaatgcaa tcttttcat aaaggaggac aaccatgaac cactctgtct cctctat        57
```

<210> SEQ ID NO 50
<211> LENGTH: 33
<212> TYPE: DNA
<213> ORGANISM: artificial sequence
<220> FEATURE:
<223> OTHER INFORMATION: synthesized

<400> SEQUENCE: 50

```
gacaactgca gtcagagatc cacgctgttc ggc                                 33
```